United States Patent
Komm et al.

(10) Patent No.: US 12,023,321 B2
(45) Date of Patent: Jul. 2, 2024

(54) LASOFOXIFENE TREATMENT OF AROMATASE-RESISTANT ER+CANCER

(71) Applicant: Sermonix Pharmaceuticals, Inc., Columbus, OH (US)

(72) Inventors: Barry Samuel Komm, Columbus, OH (US); Geoffrey L. Greene, Chicago, IL (US)

(73) Assignee: Sermonix Pharmaceuticals, Inc., Columbus, OH (US)

( * ) Notice: Subject to any disclaimer, the term of this patent is extended or adjusted under 35 U.S.C. 154(b) by 0 days.

(21) Appl. No.: 18/325,883

(22) Filed: May 30, 2023

(65) Prior Publication Data

US 2023/0321035 A1    Oct. 12, 2023

Related U.S. Application Data

(63) Continuation of application No. 17/989,382, filed on Nov. 17, 2022, now abandoned.

(60) Provisional application No. 63/280,769, filed on Nov. 18, 2021.

(51) Int. Cl.
*A61K 31/40* (2006.01)
*A61K 31/4155* (2006.01)
*A61K 45/06* (2006.01)
*A61P 35/00* (2006.01)

(52) U.S. Cl.
CPC .......... *A61K 31/40* (2013.01); *A61K 31/4155* (2013.01); *A61K 45/06* (2013.01); *A61P 35/00* (2018.01)

(58) Field of Classification Search
CPC ................................ A61K 31/40; A61P 35/00
See application file for complete search history.

(56) References Cited

U.S. PATENT DOCUMENTS

| | | | |
|---|---|---|---|
| 5,552,412 | A | 9/1996 | Cameron et al. |
| 5,948,809 | A | 9/1999 | Chiu et al. |
| 6,060,503 | A | 5/2000 | Labrie et al. |
| 6,107,331 | A | 8/2000 | MacLean et al. |
| 6,153,622 | A | 11/2000 | Cameron et al. |

(Continued)

FOREIGN PATENT DOCUMENTS

| | | |
|---|---|---|
| AU | 2017360365 B2 | 8/2022 |
| CA | 3040266 A1 | 5/2018 |

(Continued)

OTHER PUBLICATIONS

Benor (Molecular Oncology vol. 14 pp. 1640-1652 published 2020). (Year: 2020).*

(Continued)

*Primary Examiner* — Theodore R. Howell
*Assistant Examiner* — George W Kosturko
(74) *Attorney, Agent, or Firm* — Fenwick & West LLP

(57) ABSTRACT

The disclosure provides methods for treating estrogen receptor positive (ER+) cancer in a patient who has progressed on an aromatase inhibitor. Of particular interest are ER+ cancers that do not harbor a gain of function missense mutation within the ligand binding domain (LBD) of the Estrogen Receptor 1 (ESR1) gene. The provided methods involve the administration of an effective amount of lasofoxifene, a pharmaceutically acceptable salt, prodrug or functional derivative thereof.

30 Claims, 16 Drawing Sheets

(56) References Cited

U.S. PATENT DOCUMENTS

Figure 1:
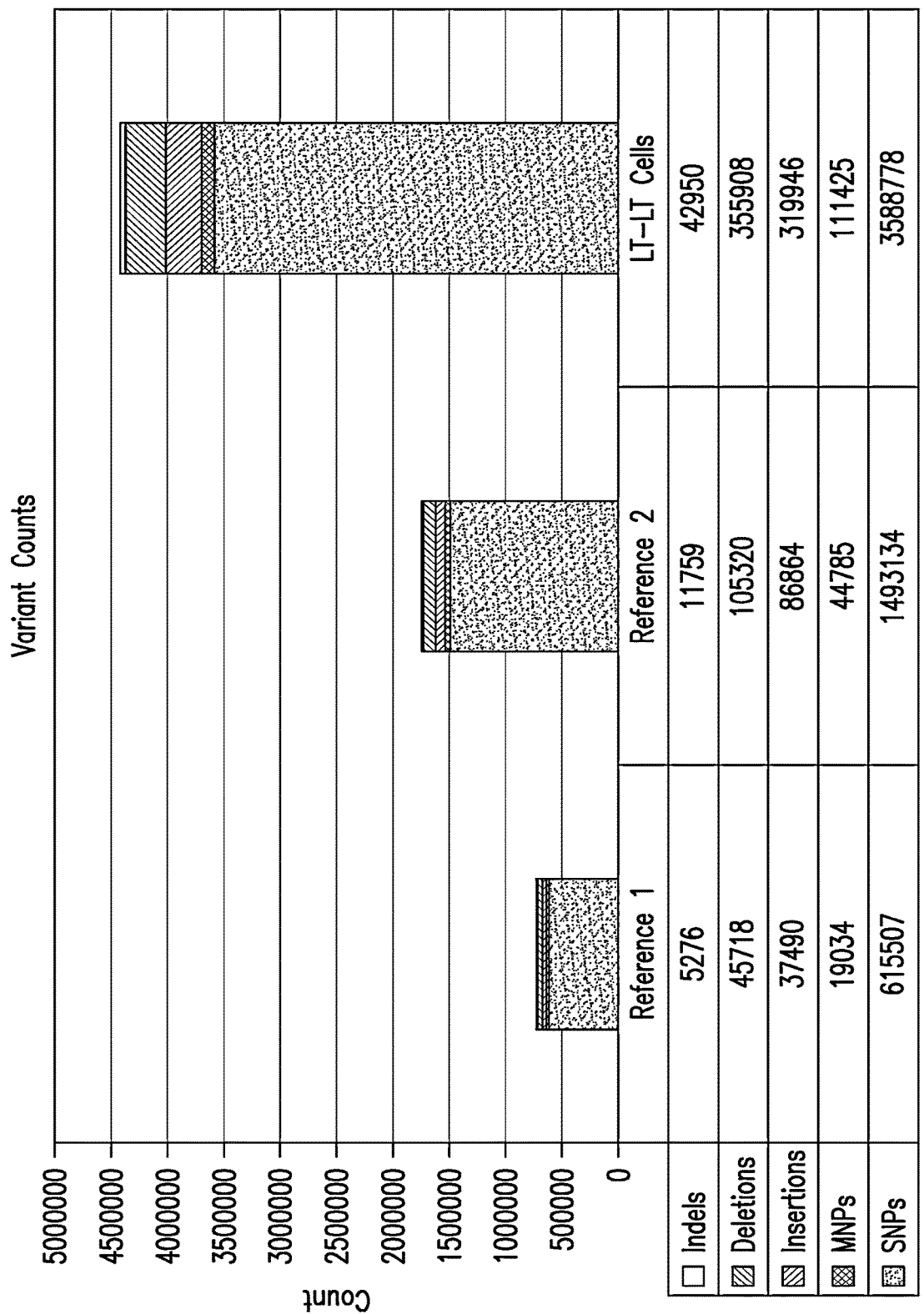

| | | |
|---|---|---|
| 6,204,286 B1 | 3/2001 | Cameron et al. |
| 6,232,476 B1 | 5/2001 | Chiu |
| 6,274,618 B1 | 8/2001 | MacLean et al. |
| 6,323,232 B1 | 11/2001 | Ke et al. |
| 6,323,345 B1 | 11/2001 | Chiu |
| 6,355,670 B1 | 3/2002 | Maclean et al. |
| 6,395,911 B1 | 5/2002 | Chiu |
| 6,403,611 B2 | 6/2002 | Maclean et al. |
| 6,436,977 B1 | 8/2002 | Thompson |
| 6,441,193 B1 | 8/2002 | Cameron et al. |
| 6,511,986 B2 | 1/2003 | Zhang et al. |
| 6,512,002 B2 | 1/2003 | Lee et al. |
| 6,613,796 B2 | 9/2003 | Maclean et al. |
| 6,906,202 B2 | 6/2005 | McLaughlin et al. |
| 6,911,456 B2 | 6/2005 | MacLean et al. |
| RE39,558 E | 4/2007 | Cameron et al. |
| 7,255,984 B2 | 8/2007 | Ke et al. |
| 7,358,374 B2 | 4/2008 | McLaughlin et al. |
| 7,553,500 B2 | 6/2009 | Gierer |
| 9,018,244 B2 | 4/2015 | Kushner et al. |
| 9,204,286 B1 | 12/2015 | Annan et al. |
| 10,231,978 B2 | 3/2019 | Yang et al. |
| 10,258,604 B2 | 4/2019 | Andreano et al. |
| 10,624,874 B2 | 4/2020 | Yang et al. |
| 10,905,659 B2 | 2/2021 | Andreano et al. |
| 11,497,730 B2 | 11/2022 | Andreano et al. |
| 2001/0025051 A1 | 9/2001 | Cameron et al. |
| 2002/0132816 A1 | 9/2002 | Cameron et al. |
| 2003/0040510 A1 | 2/2003 | Labrie |
| 2003/0114440 A1 | 6/2003 | Lee et al. |
| 2004/0009994 A1 | 1/2004 | MacLean et al. |
| 2004/0044080 A1 | 3/2004 | Place et al. |
| 2004/0053898 A1 | 3/2004 | Fritzemeier et al. |
| 2004/0057992 A1 | 3/2004 | Gierer |
| 2004/0110689 A1 | 6/2004 | Garnick |
| 2005/0065165 A1 | 3/2005 | Rosati |
| 2005/0148625 A1 | 7/2005 | MacLean et al. |
| 2009/0012052 A1 | 1/2009 | Coopersmith et al. |
| 2010/0256394 A1 | 10/2010 | Lustig et al. |
| 2010/0317712 A1 | 12/2010 | Cameron et al. |
| 2011/0015134 A1 | 1/2011 | Retsky |
| 2011/0182888 A1 | 7/2011 | Ordentlich et al. |
| 2012/0046199 A1 | 2/2012 | Ruijtenbeek et al. |
| 2012/0052508 A1 | 3/2012 | Bilal et al. |
| 2014/0079665 A1 | 3/2014 | Goetsch et al. |
| 2014/0080905 A1 | 3/2014 | Dalton et al. |
| 2014/0134170 A1 | 5/2014 | Garcia et al. |
| 2014/0221329 A1 | 8/2014 | Cronin et al. |
| 2015/0258080 A1 | 9/2015 | Hager et al. |
| 2015/0258099 A1 | 9/2015 | Hager et al. |
| 2015/0274640 A1 | 10/2015 | Wardell et al. |
| 2016/0038506 A1 | 2/2016 | Podolski et al. |
| 2016/0058774 A1 | 3/2016 | El-Alfy et al. |
| 2016/0145691 A1 | 5/2016 | Cronin et al. |
| 2016/0201135 A1 | 7/2016 | Cronin et al. |
| 2016/0324808 A1 | 11/2016 | Wardell et al. |
| 2017/0016073 A1 | 1/2017 | Cronin et al. |
| 2017/0027928 A1 | 2/2017 | McDonnell et al. |
| 2017/0202823 A1 | 7/2017 | Wardell et al. |
| 2017/0202854 A1 | 7/2017 | Genkin et al. |
| 2018/0049999 A1 | 2/2018 | Quay |
| 2018/0098963 A1 | 4/2018 | Andreano et al. |
| 2018/0221335 A1 | 8/2018 | Andreano et al. |
| 2019/0151286 A1 | 5/2019 | Andreano et al. |
| 2019/0231718 A1 | 8/2019 | Andreano et al. |
| 2019/0231743 A1 | 8/2019 | Portman |
| 2021/0361596 A1 | 11/2021 | Andreano et al. |
| 2022/0031658 A1 | 2/2022 | Andreano et al. |
| 2022/0133691 A1 | 5/2022 | Portman |
| 2023/0149350 A1 | 5/2023 | Komm et al. |
| 2023/0233490 A1 | 7/2023 | Andreano et al. |
| 2023/0321035 A1 | 10/2023 | Komm et al. |

FOREIGN PATENT DOCUMENTS

| | | | |
|---|---|---|---|
| CN | 106488767 A | 3/2017 | |
| CN | 110099680 B | 2/2021 | |
| CN | 112353796 A | 2/2021 | |
| CN | 112933082 A | 2/2021 | |
| EP | 1086692 A2 | 3/2001 | |
| EP | 3773524 A1 | 2/2021 | |
| EP | 4035662 A1 | 8/2021 | |
| EP | 3525774 B1 | 12/2021 | |
| IL | 265938 B | 8/2021 | |
| IL | 284875 B | 7/2022 | |
| JP | 2021073316 A | 5/2021 | |
| JP | 6892151 B2 | 6/2021 | |
| JP | 2023033415 A | 3/2023 | |
| KR | 10-2285453 B1 | 8/2021 | |
| KR | 10-2022-0151017 A | 11/2022 | |
| KR | 10-2462433 B1 | 11/2022 | |
| KR | 10-2023-0042390 A | 3/2023 | |
| MX | 387856 B | 11/2021 | |
| NZ | 752443 B | 2/2023 | |
| SG | 11201903236 S | 12/2020 | |
| TW | 201817422 A | 5/2018 | |
| TW | I729227 B | 6/2021 | |
| TW | I790672 B | 1/2023 | |
| TW | 202313005 A | 4/2023 | |
| TW | 202333666 A | 9/2023 | |
| WO | WO 96/21656 A1 | 7/1996 | |
| WO | WO 97/16434 A1 | 5/1997 | |
| WO | WO 97/31640 A1 | 9/1997 | |
| WO | WO 2008/145075 A2 | 12/2008 | |
| WO | WO 2009/137543 A2 | 11/2009 | |
| WO | WO 2010/088331 A1 | 8/2010 | |
| WO | WO 2013/056178 A2 | 4/2013 | |
| WO | WO 2015/136017 A1 | 9/2015 | |
| WO | WO 2016/176664 A1 | 11/2016 | |
| WO | WO 2018/071437 A1 | 4/2018 | |
| WO | WO 2018/071440 A1 | 4/2018 | |
| WO | WO 2018/093484 A1 | 5/2018 | |
| WO | WO-2019191891 A1 * | 6/2019 | ........... G02B 6/0011 |
| WO | WO 2019/199891 A1 | 10/2019 | |
| WO | WO 2023/059749 A1 | 4/2023 | |
| WO | WO 2023/091553 A1 | 5/2023 | |
| ZA | 2019/02454 B | 9/2022 | |

OTHER PUBLICATIONS

Andreano, K. J. et al., "Defining the molecular pharmacology of disease relevant estrogen receptor mutations for effective therapeutic targeting in breast cancer," FASEB, vol. 33, No. 1, Abstract No. 815.4, Apr. 1, 2019, one page.

Andreano, K.J. et al., "The Dysregulated Pharmacology of Clinically Relevant ESR1 Mutants is Normalized by Ligand-activated WT Receptor," Molecular Cancer Therapeutics, vol. 19, No. 7, May 7, 2020, pp. 1395-1405.

Angus, L., "ESR1 Mutations: Moving Towards Guiding Treatment Decision-Making in Metastatic Breast Cancer Patients," Cancer Treatment Reviews, 2017, pp. 33-40, vol. 52.

Bahreini, A et al., "Mutation Site and Context Dependent Effects of ESR1 Mutation in Genome-Edited Breast Cancer Cell Models," Breast Cancer Research, 2017, 19:60.

Bardia, A. et al., "Metastatic Breast Cancer with ESR1 Mutation: Clinical Management Considerations From the Molecular and Precision Medicine (MAP) Tumor Board at Massachusetts General Hospital," The Oncologist, 2016, pp. 1035-1040, vol. 21.

Baselga, J. et al., "Everolimus in Postmenopausal Hormone-Receptor-Positive Advanced Breast Cancer," NEJM, 2012, 366:520-529.

Behbod, F. et al., "An intraductal human-in-mouse transplantation model mimics the subtypes of ductal carcinoma in situ," Breast Cancer Research 11(5), R66, Sep. 7, 2009, pp. 1-11.

Berrodin, T.J. et al., "Differential Biochemical and Cellular Actions of Premarin Estrogens: Distinct Pharmacology of Bazedoxifene-Conjugated Estrogens Combination," Mol Endocrinol., Jan. 1, 2009, pp. 74-85, vol. 23, No. 1.

Bouchardy, C, et al. "Lung Cancer Mortality Risk Among Breast Cancer Patients Treated with Anti-Estrogens," Cancer, Mar. 15, 2011, pp. 1288-1295.

(56) References Cited

OTHER PUBLICATIONS

Carter, J. et al., "Baseline Characteristics and Concerns of Female Cancer Patients/Survivors Seeking Treatment at a Female Sexual Medicine Program," Support Care Cancer 23(8), Aug. 2015, pp. 2255-2265.
Chang, K.C.N. et al., "Gene Expression Profiling Studies of Three SERMs and Their Conjugated Estrogen Combinations in Human Breast Cancer Cells: Insights Into the Unique Antagonistic Effects of Bazedoxifene on Conjugated Estrogens," Journal of Steroid Biochemistry and Molecular Biology, 2010, pp. 117-124, vol. 118.
Cohen, L.A. et al., "LAS: A Novel Selective Estrogen Receptor Modulator with Chemopreventive and Therapeutic Activity in the N-Nitroso-N-Methylurea-Induced Rat Mammary Tumor Model," Cancer Research, Dec. 15, 2001, pp. 8683-8688, vol. 61.
Coleman, R. et al., "Adjuvant Bisphosphonate Treatment in Early Breast Cancer: Meta-Analyses of Individual Patient Data from Randomised Trials," Lancet, 2015, pp. 1353-1361, vol. 386.
Connor, C. E. et al., "Circumventing Tamoxifen Resistance in Breast Cancers Using Antiestrogens That Induce Unique Conformational Changes in the Estrogen Receptor," Cancer Res., 2001, 61:2917-2922.
Cummings, S.R. et al., "Lasofoxifene in Postmenopausal Women with Osteoporosis," The New England Journal of Medicine, Feb. 25, 2010, pp. 686-696, vol. 362, No. 8. [With Supplement].
Cuzick, J. et al., "Selective Oestrogen Receptor Modulators in Prevention of Breast Cancer: An Updated Meta-Analysis of Individual Participant Data," The Lancet, May 25, 2013, pp. 1827-1834, vol. 381.
Dayan, G. et al., "Tamoxifen and Raloxifene Differ in Their Functional Interactions with Aspartate 351 of Estrogen Receptor," Molecular Pharmacology, 2006, 70:579-588.
Dukelow, T. et al., "CDK4/6 Inhibitors in Breast Cancer," Anti-Cancer Drugs, 2015, pp. 788-806, vol. 26, No. 8.
Dusell, C. D. et al., "Regulation of Aryl Hydrocarbon Receptor Function by Selective Estrogen Receptor Modulators," Mol Endocrinol., 2010, 24:33-46.
European Medicines Agency, "Assessment Report for Fablyn, International Nonproprietary Name: lasofoxifene," 2009, 44 pages.
European Patent Office, Extended European Search Report and Opinion, EP Patent Application No. 19786222.0, Nov. 19, 2021, nine pages.
Fanning, S.W. et al., "Estrogen Receptor Alpha Somatic Mutations Y537S and D538G Confer Breast Cancer Endocrine Resistance by Stabilizing the Activating Function-2 Binding Conformation," eLife, 2016, pp. 1-25, vol. 5, e12792.
Fanning, S. W. et al., "Lasofoxifene Achieves Potent Anti-Tumor Activity in Hormone-Resistant Breast Tumors by Maintaining High Affinity Binding for Y537S ERα," Apr. 30, 2019, one page.
Fribbens, C. et al., "Plasma ESR1 Mutations and the Treatment of Estrogen Receptor-Positive Advanced Breast Cancer," Journal of Clinical Oncology, Sep. 1, 2016, pp. 2961-2968, vol. 34, No. 25.
Fribbens, C. et al., "Tracking evolution of aromatase inhibitor resistance with circulating tumour DNA analysis in metastatic breast cancer," Annals of Oncology, vol. 29, Oct. 4, 2017, pp. 145-153.
Gaillard, S.L. et al., "Constitutively active ESR1 mutations in gynecologic malignancies and clinical response to estrogen-receptor directed therapies," Gynecologic Oncology, vol. 154, Apr. 13, 2019, pp. 199-206.
Gardner, M. et al., "Clinical Pharmacology of Multiple Doses of Lasofoxifene in Postmenopausal Women," J Clin Pharmacol, 2006, pp. 52-58, vol. 46, No. 1.
Gelsomino, L. et al., "ESR Mutations Affect Anti-Proliferative Responses to Tamoxifen Through Enhanced Cross-Talk with IGF Signaling," Breast Cancer Res. Treat., Jun. 2016, pp. 253-265, vol. 157, No. 2.
Gennari, L., "Lasofoxifene: A new type of selective estrogen receptor modulator for the treatment of osteoporosis," Drugs Today 42(6), Jun. 2006, pp. 355-367.

Gennari, L., et al., "Selective estrogen receptor modulator (SERM) for the treatment of osteoporosis in postmenopausal women: focus on lasofoxifene," Clinical Interventions in Aging, 2010, pp. 19-29, vol. 5.
Goldstein, S.R. et al., "Postmenopausal Evaluation and Risk Reduction with Lasofoxifene (PEARL) Trial: 5-Year Gynecological Outcomes," Menopause: The Journal of The North American Menopause Society, 2011, pp. 17-22, vol. 18, No. 1.
Goss, P.E. et al., "Extending Aromatase-Inhibitor Adjuvant Therapy to 10 Years," The New England Journal of Medicine, Jun. 5, 2016, pp. 1-11.
Greene, G.L. et al., "Purification of T47D Human Progesterone Receptor and Immunochemical Characterization with Monoclonal Antibodies," Molecular Endocrinology, vol. 2, Iss. 8, Aug. 1, 1988, pp. 714-726.
Jeselsohn, R. et al., "Allele-Specific Chromatin Recruitment and Therapeutic Vulnerabilities of ESR1 Activating Mutations," Cancer Cell, 2018, 33:173-186.
Jeselsohn, R. et al., "Emergence of Constitutively Active Estrogen Receptor-.alpha. Mutations in Pretreated Advanced Estrogen Receptor-Positive Breast Cancer," Clinical Cancer Research, Apr. 1, 2014, pp. 1757-1767, vol. 20, No. 7.
Jeselsohn, R. et al., "ESR1 Mutations—A Mechanism for Acquired Endocrine Resistance in Breast Cancer," Clinical Oncology, Oct. 2015, pp. 573-583, vol. 12.
Johnston, S., "Endocrine Manipulation in Advanced Breast Cancer: Recent Advances with SERM Therapies," Clinical Cancer Research, Dec. 2001, pp. 4376s-4387s, vol. 7.
Johnston, S.R. et al., "Fulvestrant Plus Anastrozole or Placebo Versus Exemestane Alone After Progression on Non-Steroidal Aromatase Inhibitors in Postmenapausal Patients with Hormone-Receptor-Positive Locally Advanced or Metastatic Breast Cancer (SoFEA): A Composite, Multicentre, Phase 3 Ransomised Trial," The Lancet Oncology Sep. 2013, pp. 989-998, vol. 14, No. 10.
Johnston, S.R.D., "New Strategies in Estrogen Receptor-Positive Breast Cancer," Clinical Cancer Research, 2010, pp. 1979-1987, vol. 16.
Johnston, S.R.D., "Optimising the Treatment of ER+ Metastatic Breast Cancer," UK Breast Cancer Meeting, Nov. 21, 2014, 45 pages.
Jordan, V. C. et al., "Estrogen receptor mutations found in breast cancer metastases integrated with the molecular pharmacology of selective ER modulators," Journal of the National Cancer Institute, vol. 107, Iss. 6, Apr. 2, 2015, pp. 1-10.
Joseph, J.D. et al., "The Selective Estrogen Receptor Downregulator GDC-0810 is Efficacious in Diverse Models of ER+ Breast Cancer," eLife, 2016, pp. 1-34, vol. 5, e15828.
Ke, H.Z. et al., "Long-Term Treatment of Lasofoxifene Preserves Bone Mass and Bone Strength and Does Not Adversely Affect the Uterus in Ovariectomized Rats," Endocrinology, 2004, pp. 1996-2005, vol. 145, No. 4.
Ke, H.Z. et al., "Effects of CP-336, 156, a New, Nonsteroidal Estrogen Agonist/Antagonist, on Bone, Serum Cholesterol, Uterus, and Body Composition in Rat Models," Endocrinology, 1998, pp. 2068-2076, vol. 139, No. 4.
Komm, B.S. et al., "Developing a SERM: Stringent Preclinical Selection Criteria Leading to an Acceptable Candidate (WAY-140424) for Clinical Evaluation," Ann N Y Acad Sci., 2001, pp. 317-326. vol. 949.
Kuang, Y. et al., "Unraveling the clinicopathological features driving the emergence of ESR1 mutations in metastatic breast cancer," npj Breast Cancer 4:22, Aug. 2, 2018, pp. 1-10.
Lacroix, A.Z. et al., "Breast Cancer Incidence in the Randomized PEARL Trial of Lasofoxifene in Postmenopausal Osteoporotic Women," J Natl Cancer Intstl, Nov. 17, 2000, pp. 1706-1715, vol. 102, Issue 22.
Lai, A. et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts," J Med Chem., 2015, 58:4888-4904.
Laine, M. et al., "Abstract P4-02-07: Lasofoxifene as a potential treatment for aromatase inhibitor resistant ER positive breast cancer," Cancer Research 82 (4_Supplement), Feb. 15, 2022, one page.

(56) References Cited

OTHER PUBLICATIONS

Laine, M. et al., "Abstract PD7-09: Lasofoxifene decreases breast cancer lung and liver metastasis in a mammary intraductal (MIND) xenograft model of mutant ERα+ breast cancer," Cancer Research, vol. 79, Feb. 2019, pp. 1-2.

Laine, M. et al., "Lasofoxifene as a potential treatment for therapy-resistant ER-positive metastatic breast cancer," Breast Cancer Research 23:54, May 12, 2021, pp. 1-12.

Levenson, A. S. et al., "The Key to the Antiestrogenic Mechanism of Raloxifene is Amino Acid 351 (Aspartate) in the Estrogen Receptor," Cancer Res., 1998, 58:1872-1875.

Li, S. et al., "Endocrine-Therapy-Resistant ESR1 Variants Revealed by Genomic Characterization of Breast-Cancer-Derived Xenografts," Cell Reports, vol. 4, Sep. 26, 2013, pp. 1116-1130.

Lipton, A. et al., "Effect of Denosumab Versus Zoledronic Acid in Preventing Skeletal-Related Events in Patients with Bone Metastases by Baseline Characteristics," European Journal of Cancer, 2016, pp. 75-83, vol. 53.

Liu, H. et al., "Cancer stem cells from human breast tumors areinvolved in spontaneous metastases inorthotopic mouse models," Proc Natl Acad Sci U S A, vol. 107, No. 42, Oct. 19, 2010, pp. 18115-18120.

Liu, H. et al., "Structure-Function Relationships of the Raloxifene-Estrogen-Raloxifene-Estrogen Receptor-Alpha Complex for Regulating Transforming Growth Factor-Alpha Expression in Breast Cancer Cells," J Biol Chem., 2002, 277:9189-9198.

Lother, S.A. et al., "Antiestrogen Use and Survival of Women with Non-Small Cell Lung Cancer in Manitoba, Canada," Horm Cancer, 2013, pp. 270-276, vol. 4.

Ma, C.K. et al., "Mechanisms of Aromatase Inhibitor Resistance," Nat. Rev. Cancer, 2015, 15:261-275.

Martin, L.-A. et al., "Discovery of Naturally Occurring ESR1 Mutations in Breast Cancer Cell Lines Modelling Endocrine Resistance," Nat Commun., 2017, 8:1865.

Maurer, C. et al., "New Agent for Endocrine Resistance in Breast Cancer", The Breast, 2017, 12, pp. 1-11, vol. 34.

Maximov, P.Y. et al., "The Discovery and Development of Selective Estrogen Receptor Modulators (SERMs) for Clinical Practie," Current Clinical Pharmacology, 2013, pp. 135-155, vol. 8, No. 2.

Mccain, J., "First-in-Class CDK4/6 Inhibitor Palbociclib Could Usher in a New Wave of Combination Therapies for HR+, HER2− Breast Cancer," P&T, vol. 40, No. 8, Aug. 2015, pp. 511-520.

Mcdonnell, D. P. et al., "Analysis of Estrogen Receptor Function in Vitro Reveals Three Distinct Classes of Antiestrogens," Mol Endocrinol. 1995, 9:659-69.

Mcdonnell, D. P. et al., "Identification of a Negative Regulatory Function for Steroid Receptors." Proc Natl Acad Sci U S A, 1992, 89:10563-10567.

Mcdonnell, D. P., "If We Knew Then What We Know Now, Would We Have Approached the Development of Endocrine Therapies Differently?," ENDO Online 2020 Keynote Presentation, Jun. 2020, pp. 1-48.

Mcdonnell, D.P. et al., "Neomorphic ERα Mutations Drive Progression in Breast Cancer and Present a Challenge for New Drug Discovery," Cancer Cell, 2018, 33:153-155.

Mcdonnell, D.P. et al., "Oral Selective Estrogen Receptor Downregulators (SERDs), a Breakthrough Endocrine Therapy for Breast Cancer," Journal of Medicinal Chemistry, 2015, pp. 4883-4887, vol. 58, No. 12.

Mcdonnell, D.P. et al., "The Molecular Mechanisms Underlying the Pharmacological Actions of ER Modulators: Implications for New Drug Discovery in Breast Cancer," Current Opinion in Pharmacology, Dec. 2010, pp. 620-628, vol. 10, No. 6.

Merenbakh-Lamin, K. et al., "D538G Mutation in Estrogen Receptor-.alpha.: A Novel Mechanism for Acquired Endocrine Resistance in Breast Cancer," Cancer Research, Dec. 1, 2013, pp. 6856-6864, vol. 73, No. 23.

Michalsen B. T., et al., "Selective Estrogen Receptor Modulator (SERM) Lasofoxifene Forms Reactive Quinones Similar to Estradiol," Chemical Research in Toxicology, May 29, 2012, vol. 25, No. 7, pp. 1472-1483.

Miller, W.R. et al., "Understanding the Mechanisms of Aromatase Inhibitor Resistance," Breast Cancer Research, 2012, pp. 1-11, vol. 14: 201.

Mocellin, S. et al., "Breast Cancer Chemoprevention: A Network Meta-Analysis of Randomized Controlled Trials," JNCI J Natl. Cancer Inst., 2016, 9 pages, vol. 108, No. 2.

Nagel, S.C. et al., "Development of an ER Action Indicator Mouse for the Study of Estrogens, Selective ER Modulators (SERMs), and Xenobiotics," Endocrinology, 2001, pp. 4721-4728, vol. 142, No. 11.

Niu, J. et al., "Incidence and Clinical Significance of ESR1 Mutations in Heavily Pretreated Metastatic Breast Cancer Patients," OncoTargets and Therapy, Nov. 11, 2015, pp. 3323-3328, vol. 8.

Norris, J. et al., "Identification of a New Subclass of Alu DNA Repeats Which Can Function as Estrogen Receptor-dependent Transcriptional Enhancers," The Journal of Biological Chemistry, Sep. 29, 1995, pp. 22777-22782, vol. 270, No. 39.

Ottanelli, S., "Prevention and Treatment of Bone Fragility in Cancer Patient," Clinical Cases in Mineral and Bone Metabolism, 2015, pp. 116-129, vol. 12, No. 2.

Paige, L. A. et al., "Estrogen Receptor(ER) Modulators Each Induce Distinct Conformational Changes in ERa and ERb," Proc. Natl. Acad. Sci. USA, 1999, 96:3999-4004.

Parise, C.A. et al., "Breast Cancer Survival Defined by the ER/PR/HER2 Subtypes and a Surrogate Classification According to Tumor Grade and Immunohistochemical Biomarkers," Journal of Cancer Epidemiology, 2014, Article ID 469251, pp. 1-11.

Patel, H. K. et al., "Selective Estrogen Receptor Modulators (SERMs) and Selective Estrogen Receptor Degraders (SERDs) in Cancer Treatment," Pharmacol Ther., 2018, 186:1-24.

PCT International Search Report and Written Opinion, PCT Application No. PCT/US2022/050218, Mar. 17, 2023, 19 pages.

PCT International Search Report and Written Opinion, PCT Application No. PCT/US2019/026669, Jul. 10, 2019, 24 pages.

PCT International Search Report and Written Opinion, PCT Application No. PCT/US17/55974, Jan. 29, 2018, 20 pages.

PCT International Search Report and Written Opinion, PCT Application No. PCT/US2017/055971, Jan. 2, 2018, 18 Pages.

PCT International Search Report and Written Opinion, PCT Application No. PCT/US2017/055970, Mar. 14, 2018, 24 pages.

PCT Invitation to Pay Additional Fees, PCT Application No. PCT/US17/55974, Dec. 1, 2017, 3 pages.

PCT Invitation to Pay Additional Fees, PCT Application No. PCT/US2017/055970, Jan. 18, 2018, 16 pages.

Pfizer, Inc., Fablyn® (lasofoxifene tartrate) 0.5 mg Tablets. Reproductive Health Drugs Advisory Committee Briefing Document, Sep. 8, 2008. [Retrieved from the internet on Nov. 18, 2017] <URL: https://www.fda.gov/ohrms/dockets/ac/08/briefing/2008-4381b1-02-Pfizer.pdf>.

Plourde, P. V. et al., "Abstract OT1-01-02: An open-label, randomized, multi-center phase 2 study evaluating the activity of lasofoxifene relative to fulvestrant for the treatment of postmenopausal women with locally advanced or metastatic ER+/HER2− breast cancer (MBC) with an ESR1 mutation", Cancer Research 79 (4_Supplement), Feb. 15, 2019, pp. 1-3.

Pubchem, Compound Summary: Lasofoxifene, PubChem Database CID: 216416, Aug. 9, 2005, pp. 1-34, [Online] [Retrieved on May 26, 2020] Retrieved from the Internet <URL: https://pubchem.ncbi.nlm.nih.gov/compound/216416>.

Radhi, S., "Molecular Changes During Breast Cancer and Mechanisms of Endocrine Therapy Resistance," Progress in Molecular Biology and Translational Science, Chapter Twelve, 2016, pp. 539-562, vol. 144.

Razavi et al., "The Genomic Landscape of Endocrine-Resistant Advanced Breast Cancers," Cancer Cell, 2018, 34:427-438.

Robertson, J.F.R. et al., "Fulvestrant 500 mg Versus Anastrozole 1 mg for Hormone Receptor-Positive Advanced Breast Cancer (Falcon): An International, Randomised, Double-Blind, Phase 3 Trial," The Lancet, Dec. 2016, pp. 2997-3005, vol. 388, No. 10063.

(56) References Cited

OTHER PUBLICATIONS

Robinson, D.R. et al., "Activating ESR1 Mutations in Hormone-Resistant Metastatic Breast Cancer," Nature Genetics, Dec. 2013, pp. 1446-1453, vol. 45, No. 12.
Sabnis, G. et al., "Trastuzumab reverses letrozole resistance and amplifies the sensitivity of breast cancer cells to estrogen," Cancer Research 69(4), Feb. 15, 2009, pp. 1416-1428.
Santen, R.J. et al., "Modeling of the Growth Kinetics of Occult Breast Tumors: Role in Interpretation of Studies of Prevention and Menopausal Hormone Therapyy," Cancer Epidemiology, Biomarkers & Prevention, 2012, pp. 1038-1048, vol. 21.
Schiavon, G. et al., "Analysis of ESR1 Mutation in Circulating Tumor DNA Demonstrates Evolution During Therapy for Metastatic Breast Cancer," Clin. Cancer Res., 2013, 20:1757-1767.
Sefrioui, D. et al., "Short Report: Monitoring ESR1 Mutations by Circulating Tumor DNA in Aromatase Inhibitor Resistant Metastatic Breast Cancer," International Journal of Cancer, 2015, pp. 2513-2519, vol. 137.
Sflomos, G. et al., "A Preclinical Model for Erα-Positive Breast Cancer Points to the Epithelial Microenvironment as Determinant of Luminal Phenotype and Hormone Response," Cancer Cell, 2016 pp. 407-422, vol. 29.
Shelly, W. et al., "Selective Estrogen Receptor Modulators: An Update on Recent Clinical Findings," Obstetrical and Gynecological Survey, Feb. 29, 2008, pp. 163-181, vol. 63, No. 3.
Shi, Y. et al., "A Genome-Wide Association Study Identifies Two New Cervical Cancer Susceptibility Loci at 4q12 and 17q12," Nature Genetics, Aug. 2013, pp. 918-924, vol. 45, No. 8.
So, F. V. et al., "Inhibition of proliferation of estrogen receptor-positive MCF-7 human breast cancer cells by flavonoids in the presence and absence of excess estrogen," Cancer Letters, vol. 112, Jan. 1997, pp. 127-133.
Song, D. et al., "Advances in Research on Tissue Selective Effects of Selective Estrogen Receptor Modulators," Drugs & Clinic, vol. 29, No. 2, Feb. 28, 2014, pp. 206-210 (with Translation).
Song, Y. et al., "Effects of the Conjugated Equine Estrogen/Bazedoxifene Tissue-Selective Estrogen Complex (TSEC) on Mammary Gland and Breast Cancer in Mice," Endocrinology, Dec. 1, 2012, pp. 5706-5715, vol. 153, No. 12.
Spoerke, J.M. et al., "Heterogeneity and Clinical Significance of ESR1 Mutations in ER-Positive Metastatic Breast Cancer Patients Receiving Fulvestrant," Nature Communications, May 2016, pp. 1-10, vol. 13, No. 7.
Srinivasan, S. et al., "Full Antagonism of the Estrogen Receptor Without a Prototypical Ligand Side Chain," Nature Chemical Biology, Jan. 2017, pp. 1-12, vol. 13.
Stearns, V. et al., "Gene Mutation Profiling of Breast Cancers for Clinical Decision Making," JAMA Oncology, Aug. 2015, pp. 569-570, vol. 1, No. 5.
Sun, X-Z. et al., "Autocrine and paracrine actions of breast tumor aromatase. A three-dimensional cell culture study involving aromatase transfected MCF-7 and T-47D cells," The Journal of Steroid Biochemistry and Molecular Biology, vol. 63, Iss. 1-3, Sep.-Oct. 1997, pp. 29-36.
Tan, O. et al., "Management of vulvovaginal atrophy-related sexual dysfunction in postmenopausal women: an up-to-date review," Menopause 19(1), Jan. 2012, pp. 109-117.
Thomas, C. et al., "Estrogen Receptor Mutations and Functional Consequences for Breast Cancer," Trends Endocrinal Metab., Sep. 2015, pp. 467-476, vol. 26, No. 9.
Toy, W. et al., "Activating ESR1 Mutations Differentially Affect the Efficacy of ER Antagonists," Cancer Discovery, Mar. 2017, pp. 277-287, vol. 7.
Toy, W. et al., "ESR1 Ligand Binding Domain Mutations in Hormone-Resistant Breast Cancer," Nat Genet., Dec. 2013, pp. 1439-1445, vol. 45, No. 12.
Traboulsi, T. et al., "Antiestrogens: Structure Activity Relationships and Use in Breast Cancer Treatment," Journal of Molecular Endocrinology, 2017, 58:R15-R31.

Turner, N. et al., "Genetic Hegerogeneity and Cancer Drug Resistance," Lancet Oncology, Apr. 2012, pp. e178-e185, vol. 13.
Tzukerman, M. T. et al., "Human Estrogen Receptor Transactivational Capacity is Determined by Both Cellular and Promoter Context and Mediated by Two Functionally Distinct Intramolecular Regions," Mol Endocrinol., 1994, 8:21-30.
United States Office Action, U.S. Appl. No. 16/341,027, Apr. 7, 2021, 11 pages.
Vajdos, F.F. et al., "The 2.0 .ANG. Crystal Structure of the ER.alpha. Ligand-Binding Domain Complexed with Lasofoxifene," Protein Science, 2007, pp. 897-905, vol. 16.
Wang, P. et al., "Sensitive Detection of Mono- and Polyclonal esr1 Mutations in Primary Tumors, Metastatic Lesions, and Cell-Free DNA of Breast Cancer Patients," Clin Cancer Res., 2016, 22:1130-1137.
Wang, X-N. et al., "Lasofoxifene Enhances Vaginal Mucus Formation Without Causing Hypertrophy and Increases Estrogen Receptor .beta. and Androgen Receptor in Rats," Menopause: The Journal of The North American Menopause Society, 2006, pp. 609-620, vol. 13, No. 4.
Wardell, S.E. et al., "Bazedoxifene Exhibits Antiestrogenic Activity in Animal Models of Tamoxifen-Resistant Breast Cancer: Implications for Treatment of Advanced Disease," Clinical Cancer Research, 2013, pp. 2420-2431, vol. 19.
Wardell, S. E. et al., "Effects of G1 T48, a novel orally bioavailable selective estrogen receptor degrader (SERO), and the CDK4/6 inhibitor, G1T38, on tumor growth in an animal model oftamoxifen resistant breast cancer," Proceeding of the AACR Annual Meeting, Jul. 31, 2017, one page.
Wardell, S.E. et al., "Efficacy of SERD/SERM Hybrid-CDK4/6 Inhibitor Combinations in Models of Endocrine Therapy-Resistant Breast Cancer," Clinical Cancer Research, Nov. 15, 2015, pp. 5121-5130, vol. 21, No. 22.
Wardell, S. E. et al., "Evaluation of the pharmacological activities of RAD1901, a selective estrogen receptor degrader," Endocr Relat Cancer 22(5), Oct. 2015, pp. 713-724.
Wardell, S.E., et al., "From empirical to mechanism-based discovery of clinically useful Selective Estroaen Receptor Modulators (SERMs)," Steroids, 2014, pp. 30-38, vol. 90.
Wardell, S.E. et al., "The Turnover of Estrogen Receptor a by the Selective Estrogen Receptor Degrader (SERD) Fulvestrant is a Saturable Process That is not Required for Antagonist Efficacy," Biochem Pharmacol., Jul. 15, 2011, pp. 122-130, vol. 82, No. 2.
Wijayaratne, A. L. et al., "Comparative Analyses of the Mechanistic Differences Among Antiestrogens," Endocrinology, 1999, 140: 5828-5840.
Wurz, G.T. et al., "Ospemifene, vulvovaginal atrophy and breast cancer," Maturitas, vol. 74, Mar. 2013, pp. 220-225.
Zhang, Y. et al., "Breast Cancer Index Identifies Early-Stage Estrogen Receptor-Positive Breast Cancer Patients at Risk for Early- and Late-Distant Recurrence," Clinical Cancer Research 19(15), Jun. 11, 2013, pp. 4196-4205.
Zundelevich, A. et al., "ESR1 Mutations Are Frequent in Newly Diagnosed Metastatic and Loco-Regional Recurrence of Endocrine-Treated Breast Cancer and Carry Worse Prognosis," Breast Cancer Research 22(1):16, Feb. 2020, pp. 1-11.
Anzano, M. A. et al., "Chemoprevention of mammary carcinogenesis in the rat: combined use of raloxifene and 9-cis retinoic acid," Journal of the National Cancer Institute, vol. 88, No. 2, Jan. 17, 1996, pp. 123-125.
Beith, J. et al., "Hormone receptor positive, HER2 negative metastatic breast cancer: A systematic review of the current treatment landscape," Asia-Pacific Journal of Clinical Oncology 12(Suppl. 1), Mar. 2016, pp. 3-18.
Capen, C.C. "Toxic responses of the endocrine system," Casarett & Doull's Toxicology; The Basic Science of Poisons, 6th ed. New York: McGraw-Hill, 2001, pp. 711-760.
Cline, J.M. et al., "Assessment of hormonally-active agents in the reproductive tract of female nonhuman primates," Toxicologic Pathology, vol. 29, No. 1, Jan. 2001, pp. 84-90.
clinicaltrials.gov, "NCT03781063: Evaluation of Lasofoxifene Versus Fulvestrant in Advanced or Metastatic ER+/HER2− Breast

(56) References Cited

OTHER PUBLICATIONS

Cancer With an ESR1 Mutation," including History of Changes for Study: NCT03781063, Dec. 14, 2018, pp. 1-19.
clinicaltrials.gov, "NCT04432454: Evaluation of Lasofoxifene Combined With Abemaciclib in Advanced or Metastatic ER+/HER2− Breast Cancer With an ESR1 Mutation (ELAINEII)," Including History of Changes for Study, Jun. 16, 2020, pp. 1-9.
Cummings, S.R. et al., "The Effect of Raloxifene on Risk of Breast Cancer in Postmenopausal Women: Results from the MORE Randomized Trial," Multiple Outcomes of Raloxifene Evaluation. JAMA, 1999:2189-97.
Dorrington, J.H. et al., "Interactions between FSH, estradiol-17 beta and transforming growth factor-beta regulate growth and differentiation in the rat gonad," J Steroid Biochem Molecular Biol., vol. 44, No. 4-6, 1993, pp. 441-447.
Eli Lilly and Company, "FDA Review Document; Pharmacology/Toxicology Review of NDA Submission for Raloxifene hydrochloride (Evista™)," Application No. 020815, Nov. 21, 1997, pp. 83-136.
Eli Lilly and Company, "Lilly Announces Phase 3 MONARCH 2 Breast Cancer Study of Abemaciclib Met Primary Endpoint of Progression-Free Survival," Mar. 20, 2017, pp. 1-3.
Fisher, B. et al., "Tamoxifen for Prevention of Breast Cancer: Report of the National Surgical Adjuvant Breast and Bowel Project P-1 Study," Journal of the National Cancer Institute, vol. 90, No. 18, Sep. 16, 1998, pp. 1371-1388.
Gervaso, L. et al., "Venous thromboembolism in breast cancer patients receiving cyclin-dependent kinase inhibitors," Journal of Thrombosis and Haemostasis, vol. 18, Iss. 1, Jan. 2020, pp. 162-168.
Goldstein, S.R. et al., "Adverse events that are associated with the selective estrogen receptor modulator levormeloxifene in an aborted phase III osteoporosis treatment study," American Journal of Obstetrics and Gynecology, vol. 187, Iss. 3, Sep. 2002, pp. 521-527.
Goldstein, S.R. et al., "Ospemifene 12-month safety and efficacy in postmenopausal women with vulvar and vaginal atrophy," Ospemifene Study Group, Climacteric 17(2), Nov. 23, 2013, pp. 173-182.
Gottardis, M.M et al., "Antitumor Actions of Keoxifene and Tamoxifen in the N-Nitrosomethylurea-induced Rat Mammary Carcinoma Model," Cancer Research, vol. 47, Iss. 15, Aug. 1987, pp. 4020-4024.
Gregson, R.L. et al., "Spontaneous Ovarian Neoplasms of the Laboratory Rat," Vet Pathol., vol. 21, 1984, pp. 292-299.
Hamilton, E. et al., "nextMONARCH Phase 2 randomized clinical trial: overall survival analysis of abemaciclib monotherapy or in combination with tamoxifen in patients with endocrine-refractory HR+, HER2− metastatic breast cancer," Breast Cancer Research and Treatment, vol. 195, Jul. 12, 2022, pp. 55-64.
Hart, J.E., "Endocrine pathology of estrogens: Species differences," Pharmacology & Therapeutics, vol. 47, Iss. 2, 1990, pp. 203-218.
Hendrick Ellenson, L. et al., "Chapter 8: Precursors of Endometrial Carcinoma: Endometrial Hyperplasia and Related Cellular Changes," Blaustein's Pathology of the Female Genital Tract, R.J. Kurman, Editor. Jul. 2, 2019, Springer Nature Switzerland, pp. 439-472.
Heywood, R. et al., "The Experimental Toxicology of Estrogens," Pharmacology & Therapeutics, vol. 8, Iss. 1, 1980, pp. 125-142.
Hill, A.B., "The Environment and Disease: Association or Causation?," Proceedings of the Royal Society of Medicine 58(5), 1965, pp. 295-300.
Horsted, F. et al., "Risk of Venous Thromboembolism in Patients with Cancer: A Systematic Review and Meta-Analysis," PLoS Medicine 9(7), Jul. 31, 2021, pp. 1-19.
FDA Label, Ibrance® (palbociclib) tablets, Pfizer Inc., Initial U.S. Approval in 2015, New York, New York, 27 pages.
Jeselsohn, R. et al., "The Evolving Role of the Estrogen Receptor Mutations in Endocrine Therapy-Resistant Breast Cancer," Curr Oncol Rep. 19(5), Apr. 3, 2017, pp. 1-8.
Kendall, M.E. et al., "The effects of diethylstilbestrol, tamoxifen, and toremifene on estrogen-inducible hepatic proteins and estrogen receptor proteins in female rats," Toxicology and Applied Pharmacology, vol. 144, Iss. 1, May 1992, pp. 127-131.
FDA Label, Kisqali® (ribociclib) tablets, Novartis Pharmaceuticals Corporation, Initial U.S. Approval in 2017, East Hanover, New Jersey, 30 pages.
Lupini, L. et al., "High-sensitivity assay for monitoring ESR1 mutations in circulating cell-free DNA of breast cancer patients receiving endocrine therapy," Nature Scientific Reports 8(4371), Mar. 12, 2018, pp. 1-10.
Morrell, J.A. et al., "Studies on Stilbestrol I. Some Effects of Continuous Injections of Stilbestrol in the Adult Female Rat," Endocrinology, vol. 29, Iss. 5, Nov. 1941, pp. 796-808.
FDA Label, Orserdu™ (elacestrant) tablets, Stemline Therapeutics, Inc., Initial U.S. Approval in 2023, New York, New York, 14 pages.
Pinkerton, J.V. et al. "Effects of Bazedoxifene/Conjugated Estrogens on the Endometrium and Bone: A Randomized Trial," The Journal of Clinical Endocrinology & Metabolism, vol. 99, Iss. 2, Feb. 2014, pp. E189-E198.
FDA Label, Piqray® (alpelisib) tablets, Novartis Pharmaceuticals Corporation, Initial U.S. Approval in 2019, East Hanover, New Jersey, 22 pages.
Rugo, H.P. et al., "Management of Abemaciclib-Associated Adverse Events in Patients with Hormone Receptor-Positive, Human Epidermal Growth Factor Receptor 2-Negative Advanced Breast Cancer: Safety Analysis of MONARCH 2 and MONARCH 3," The Oncologist 26(1), Jan. 2021, pp. e53-e65.
Smyth, L.M. et al., "Capivasertib, an AKT Kinase Inhibitor, as Monotherapy or in Combination with Fulvestrant in Patients with $AKT1^{E17K}$-Mutant, ER-Positive Metastatic Breast Cancer," Clinical Cancer Research 26(15), Aug. 1, 2020, pp. 3947-3957.
Styles, J.A. et al., "Clastogenic and aneugenic effects of tamoxifen and some of its analogues in hepatocytes from dosed rats and in human lymphoblastoid cells transfected with human P450 cDNAs (MCL-5 cells)," Carcinogenesis, vol. 18, No. 2, 1997, pp. 303-313.
United States Office Action, U.S. Appl. No. 17/989,382, Jun. 21, 2023, 15 pages.
United States Office Action, U.S. Appl. No. 18/193,207, Jun. 23, 2023, 26 pages.
FDA Label, Verzenio® (abemaciclib) tablets, Lilly USA, LLC, Initial U.S. Approval in 2017, Indianapolis, Indiana, 31 pages.
Watson, N.W. et al., "Venous and arterial thrombosis associated with abemaciclib therapy for metastatic breast cancer," Cancer, vol. 128, Iss. 17, Jun. 29, 2022, pp. 3224-3232.

* cited by examiner

LASOFOXIFENE TREATMENT OF AROMATASE-RESISTANT ER+CANCER

1. CROSS-REFERENCE TO RELATED APPLICATIONS

This application claims benefit of and priority to U.S. application Ser. No. 17/989,382, filed Nov. 17, 2022, which claims benefit of and priority to U.S. Provisional Application No. 63/280,769, filed Nov. 18, 2021, the disclosure of each of which is incorporated herein by reference in its entirety.

2. BACKGROUND OF THE INVENTION

Estrogen receptor positive ($ER^+$) breast cancers are those that express estrogen receptor α ($ERα$), which is encoded by the ESR1 gene. Approximately 70% of breast cancers are $ER^+$ and are, therefore, treated with agents that deplete circulating estrogen levels or that block estrogen signaling in the cancer cell (collectively, endocrine therapy). Selective estrogen receptor modulators (SERMs), selective estrogen receptor degraders (SERDs), and aromatase inhibitors (AIs) are the major classes of endocrine therapy agents. Endocrine therapy has led to significant improvement in outcome of women with $ER^+$ breast cancer. However, the effectiveness of endocrine therapies is limited by intrinsic, and importantly, by acquired endocrine resistance. In response to the selective pressure imposed by endocrine therapies, in particular by aromatase inhibitors, $ER^+$ tumors evolve various escape mechanisms. Among these is acquisition of gain-of-function mutations in the ESR1 gene that alter the ligand binding domain of the $ERα$ receptor, rendering the receptor constitutively active at low levels, or in the absence, of estrogen. Despite the benefits of endocrine therapy, the majority of patients with $ER^+$ will eventually acquire resistance and progress.

Lasofoxifene, a selective estrogen receptor modulator (SERM), was shown to reduce the risk of $ER^+$ breast cancer in women with wild estrogen receptors, post-menopausal women with no history of breast cancer being treated with osteoporosis. LaCroix et al., *J. Natl. Cancer Inst.* 102:1706-1715 (2010). Lasofoxifene was later shown to retain the ability to inhibit progression of $ER^+$ cancers that have developed gain-of-function mutations in the ligand binding domain of the $ERα$ receptor. U.S. patent. Nos. 10,258,605; 10,905,659; WO 2019/199891. The efficacy of lasofoxifene as a single agent in the treatment of premenopausal and postmenopausal women with locally advanced or metastatic $ER^+$ breast cancers that have acquired ESR1 gain-of-function mutations is currently being confirmed in a phase 2 clinical trial, NCT03781063 (the ELAINE trial). A clinical trial confirming the efficacy of lasofoxifene in combination with the CDK 4/6 inhibitor, abemaciclib, in a similar population of breast cancer patients, all of whom have gain-of-function mutations in the $ERα$ receptor, is also underway, NCT04432454 (the ELAINE II trial).

Although lasofoxifene has been shown to be effective in inhibiting progression of $ER^+$ breast cancers that have progressed on endocrine therapy through acquisition of ESR1 gain-of-function mutations, $ER^+$ cancer cells evolve other mechanisms by which to circumvent endocrine therapies. There thus remains a need for therapeutic agents that are effective in inhibiting progression and metastasis of $ER^+$ cancers that progress on endocrine therapy and that lack mutations of the ESR1 gene.

3. SUMMARY OF THE INVENTION

In vitro and animal model experiments newly demonstrate that lasofoxifene is more effective than fulvestrant (ICI) in a letrozole-induced, AI-resistant breast tumor model (MCF-7 LTLT cells) that does not express $ERα$ activating mutations. These data demonstrate that lasofoxifene is an effective therapy for AI resistant $ER^+$ cancers that do not express $ERα$ activating mutations.

Accordingly, in a first aspect, methods are provided for reducing the progression of estrogen receptor positive ($ER^+$) cancer in a patient who has progressed on an aromatase inhibitor, wherein the cancer does not have a gain of function missense mutation within the ligand binding domain (LBD) of the Estrogen Receptor 1 (ESR1) gene. The method comprises administering to the patient an effective amount of lasofoxifene or a pharmaceutically acceptable salt, prodrug, or functional derivative thereof.

In some embodiments, the $ER^+$ cancer is locally advanced or metastatic breast cancer, optionally wherein the cancer is HER2−.

In some embodiments, the aromatase inhibitor is exemestane (Aromasin®), letrozole (Femara®), or anastrozole (Arimidex®).

In some embodiments, the method further comprises the earlier step of: determining that the cancer does not have a gain of function missense mutation within the ligand binding domain (LBD) of the Estrogen Receptor 1 (ESR1) gene.

In some embodiments, lasofoxifene is administered as lasofoxifene tartrate.

In some embodiments, lasofoxifene is administered by oral, intravenous, transdermal, vaginal topical, or vaginal ring administration.

In some embodiments, lasofoxifene is administered by oral administration. In certain of these embodiments, lasofoxifene is administered orally in a dose of 5 mg/day to about 10 mg/day.

In some embodiments, the method further comprises treating said patient with at least one additional endocrine therapy.

In some embodiments, the method further comprises administering an effective amount of cyclin-dependent kinase 4/6 (CDK4/6) inhibitor. In certain embodiments, the CDK4/6 inhibitor is palbociclib, abemaciclib, or ribociclib. In some embodiments, the CDK4/6 inhibitor is abemaciclib.

In some embodiments, the method further comprises administering an effective amount of an AKT inhibitor. In certain embodiment, the AKT inhibitor is afuresertib.

In some embodiments, the method further comprises administering an effective amount of an mTor inhibitor.

4. BRIEF DESCRIPTION OF THE DRAWINGS

These and other features, aspects, and advantages of the present invention will become better understood with regard to the following description, and accompanying drawings, where:

FIG. 1 shows a comparison of variant counts in the AI resistant breast tumor model MCF-7 LTLT cells versus two publicly available reference genomes of MCF7 "WT" from the literature.

Figure 2:
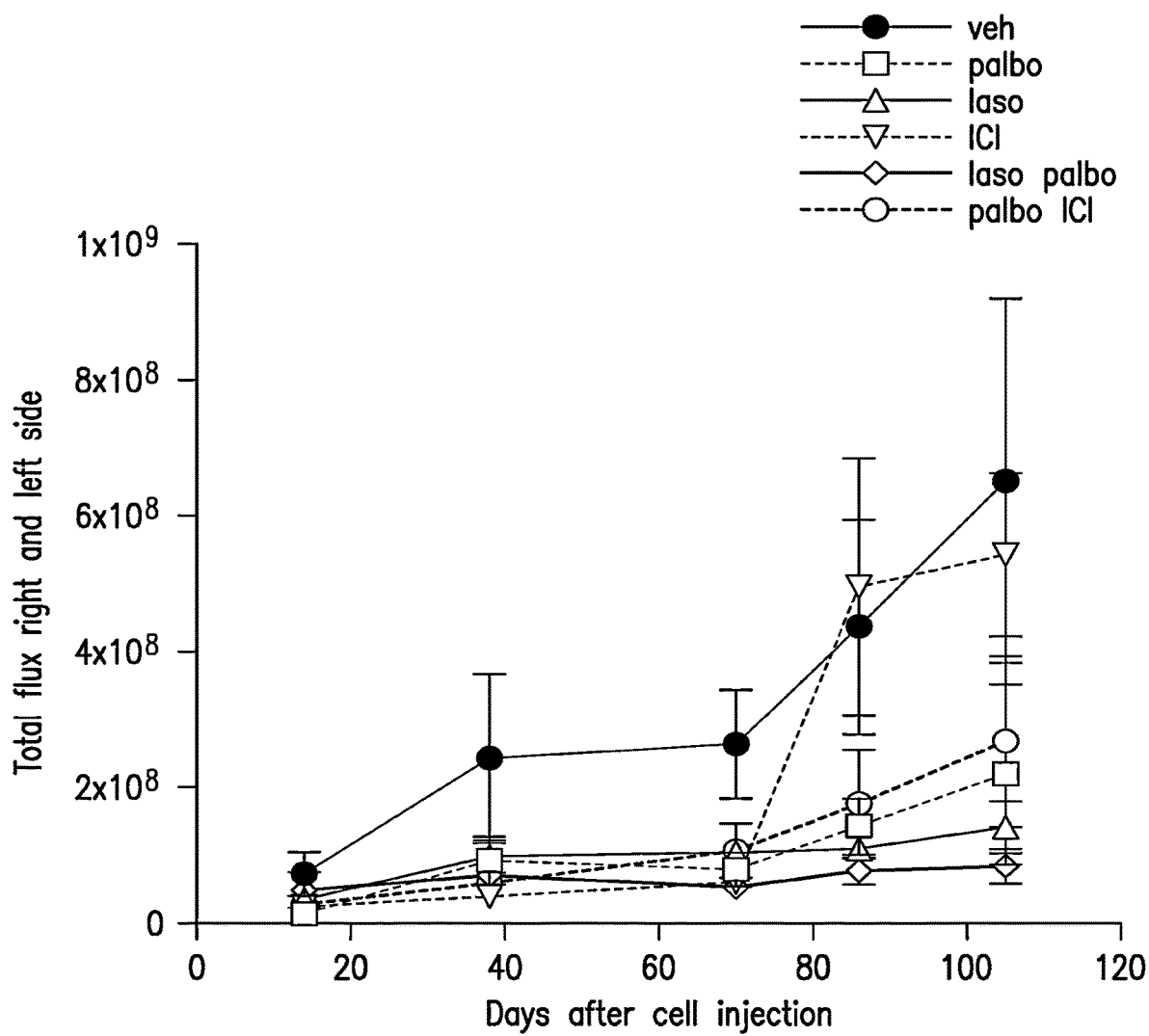

FIG. 2 presents data showing that lasofoxifene inhibits primary tumor growth of MCF7 LTLT (AI-resistant, $ER^+$, cells lacking ESR1 gain-of-function mutations) tumors. The data are from in vivo imaging showing the total photon flux quantified with the live image software over time for each group. Mice were treated with vehicle, palbociclib, lasofoxifene, fulvestrant (ICI), lasofoxifene+palbociclib, or fulvestrant (ICI)+Palbociclib.

Figure 3:
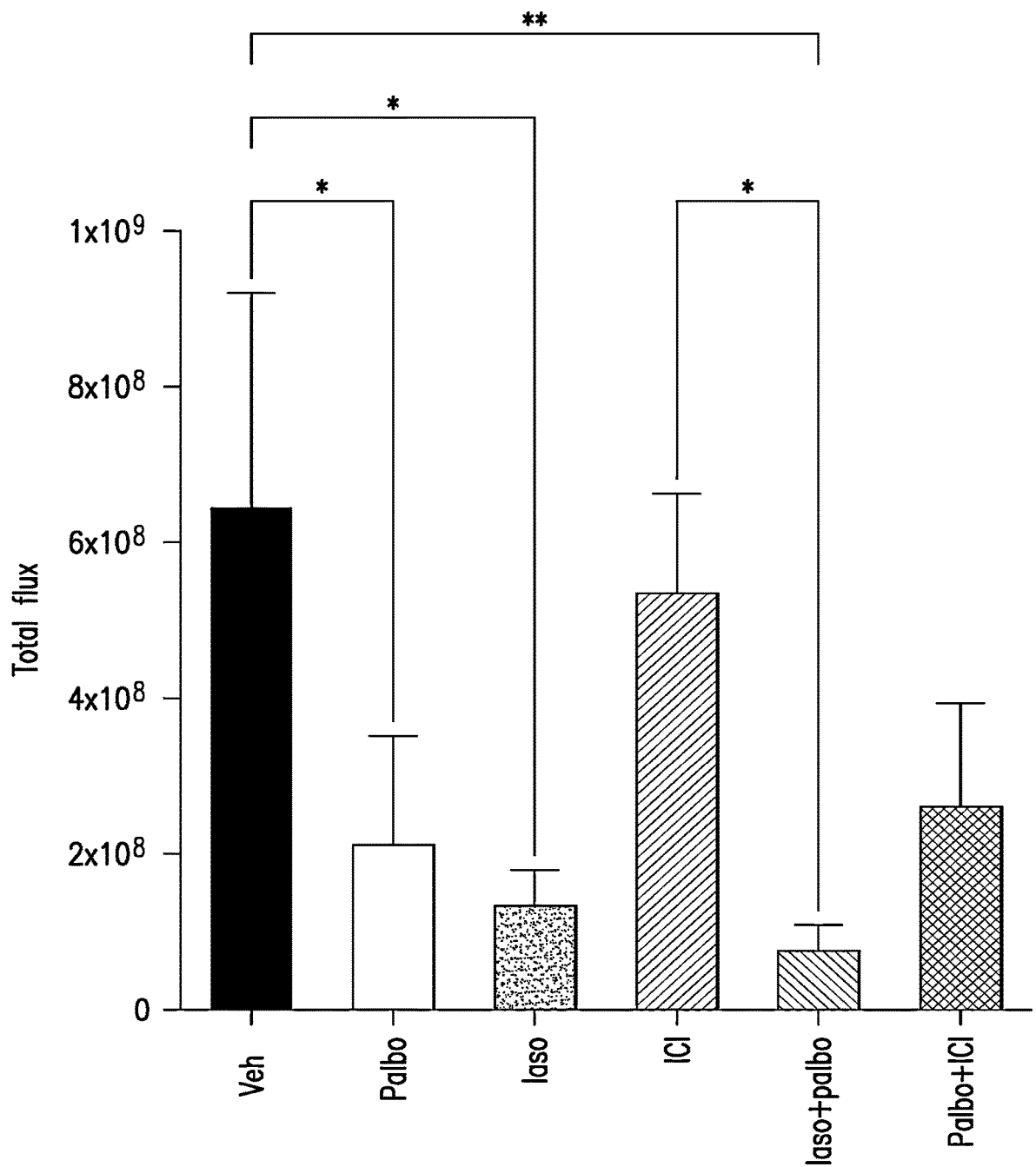

FIG. 3 is a histogram summarizing data showing that lasofoxifene inhibits primary tumor growth in AI-resistant ER+ cells lacking ESR1 gain-of-function mutations. The histogram shows the total photon flux of the mammary glands at day 104. N=6-12 glands+/− SEM. P values are: * p<0.05,  p<0.005, *p<0.0005, ****p<0.0001.

Figure 4:
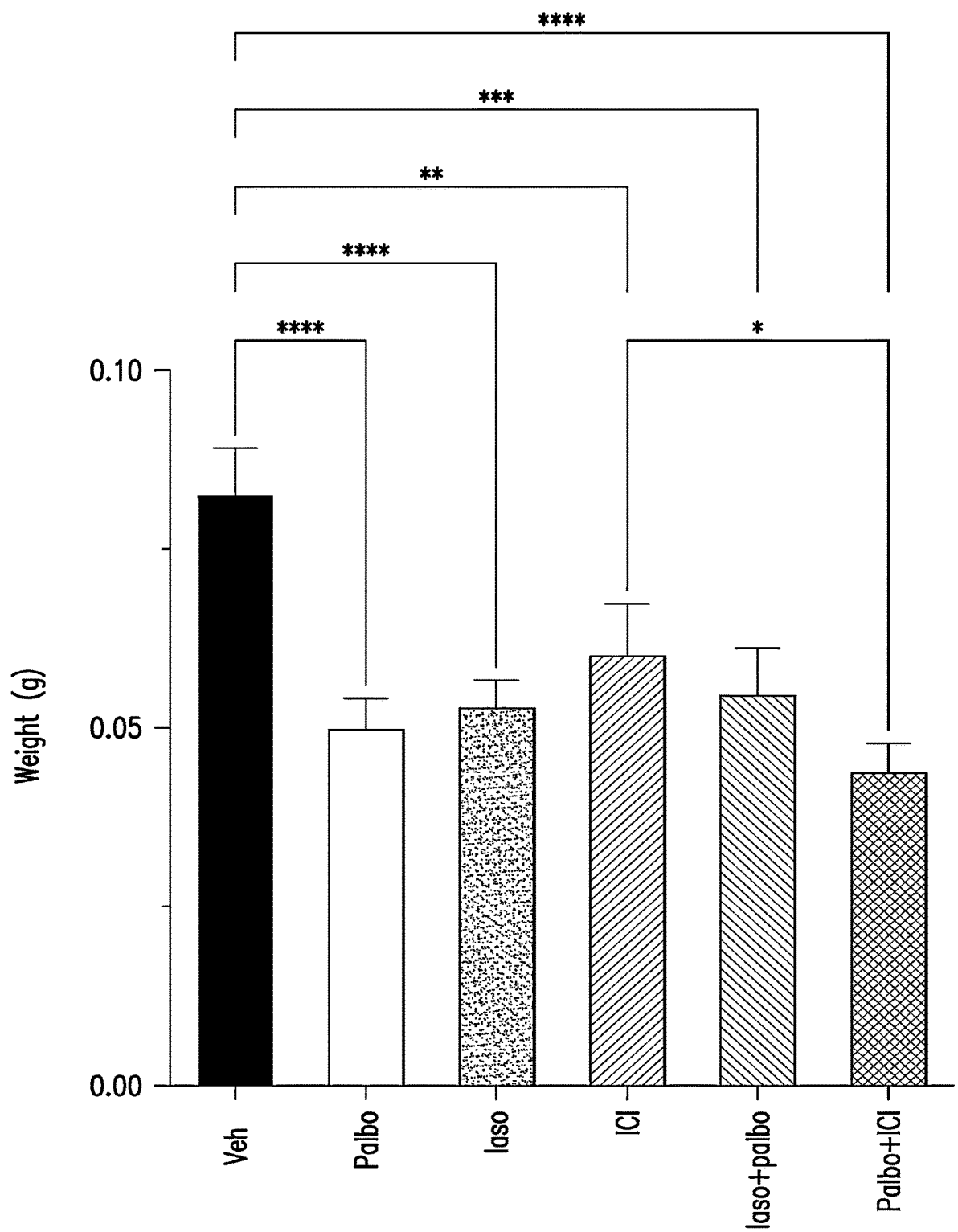

FIG. 4 presents data showing that lasofoxifene inhibits increases in primary tumor weight in AI-resistant, ER+ cells lacking ESR1 gain-of-function mutations. The histogram shows the average weight of the mammary gland at day of sacrifice. N=6-12 glands+/− SEM. P values are: * p<0.05,  p<0.005, *p<0.0005, ****p<0.0001.

Figure 5:
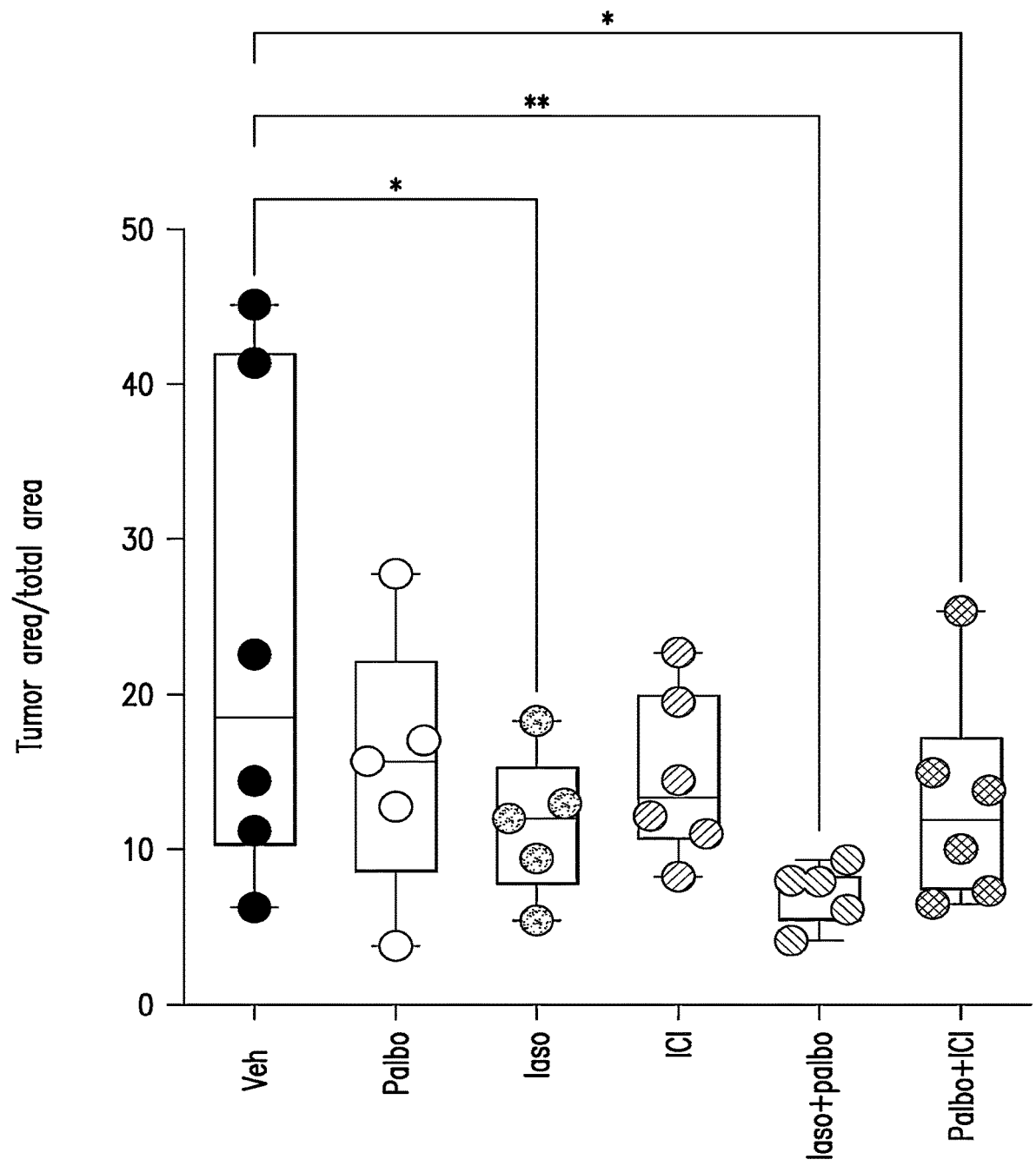

FIG. 5 presents data showing that tumor area is reduced by lasofoxifene and lasofoxifene+palbociclib. Percent tumor area vs total gland area as revealed via H&E analysis of cut sections of mammary glands. Histogram showing the percent of tumor area over total gland area of a H&E section. N=3-6 glands+/− SEM. P values are: * p<0.05,  p<0.005, *p<0.0005, ****p<0.0001.

Figure 6A:
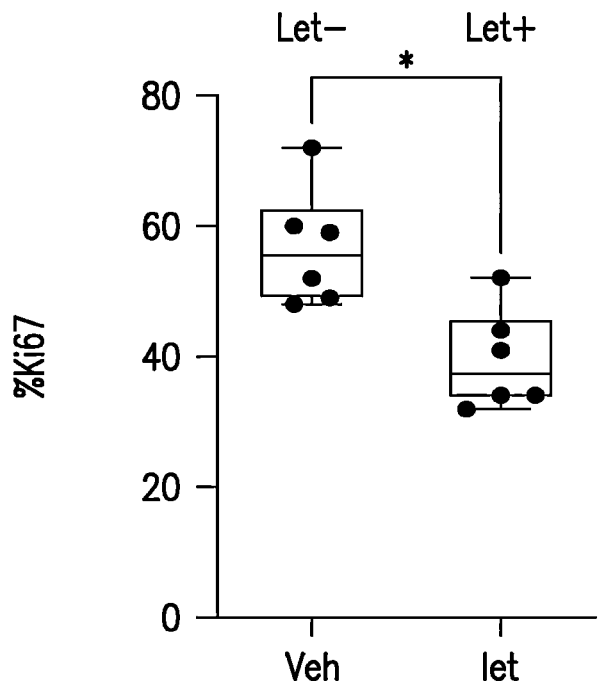
Figure 6B:
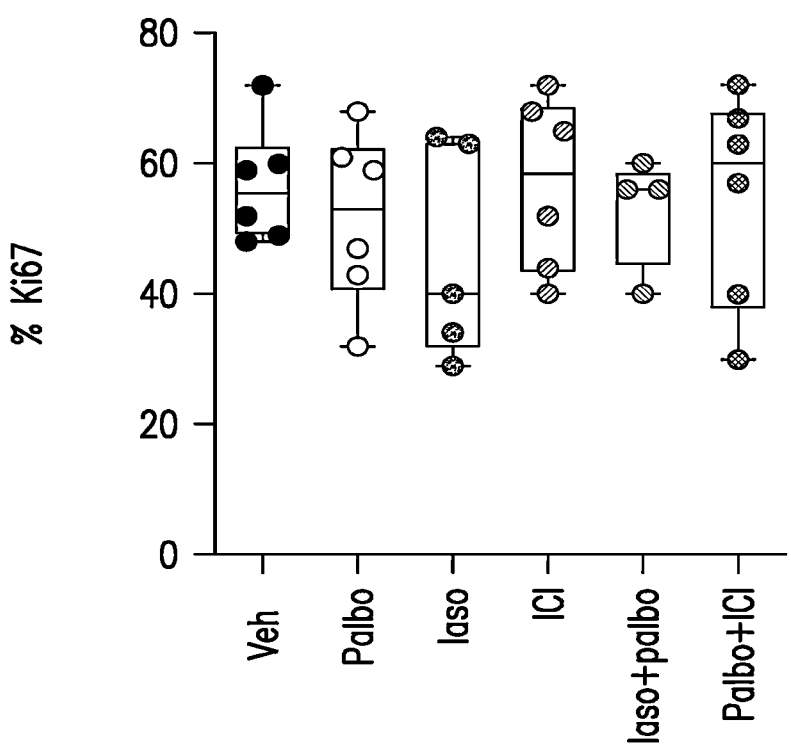
Figure 6C:
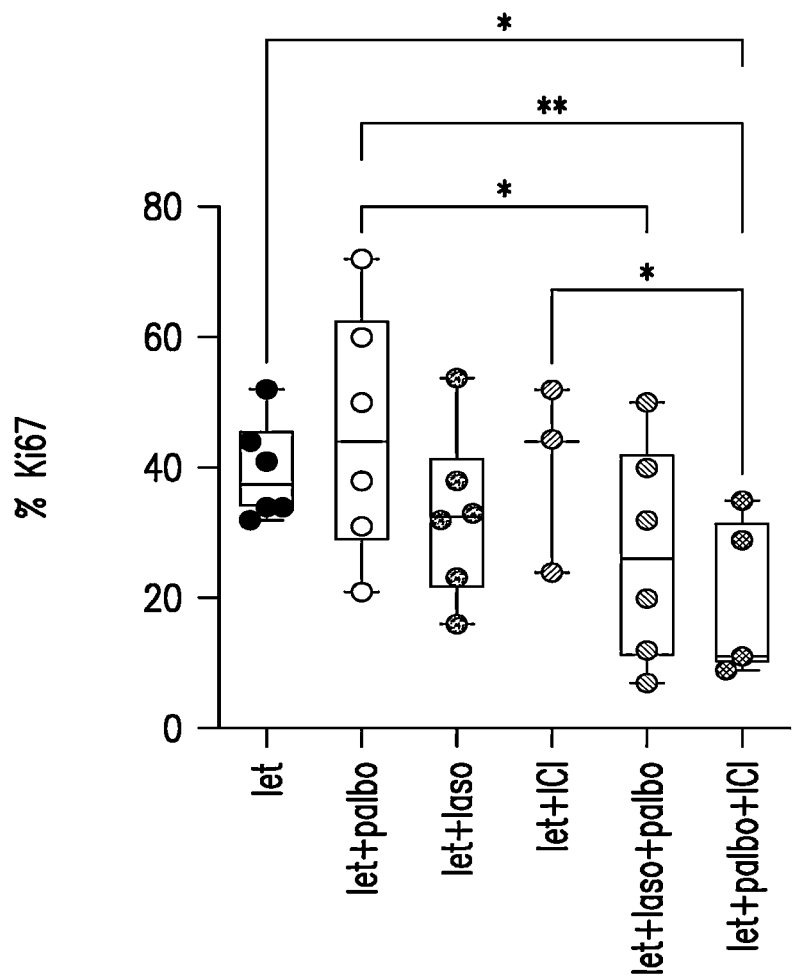

FIGS. 6A-6C present data showing that lasofoxifene reduces Ki67 proliferation index as a single agent and in combination with palbociclib in the Let+ cohort. FIG. 6A. shows % Ki67 in a comparison of vehicle versus the Let− versus Let+ cohorts. FIG. 6B and FIG. 6C, show the % Ki67 for the Let− and Let+ cohorts, respectively. N=3-6 glands+/− SEM. P values are: * p<0.05,  p<0.005, *p<0.0005, ****p<0.0001.

Figure 7A:
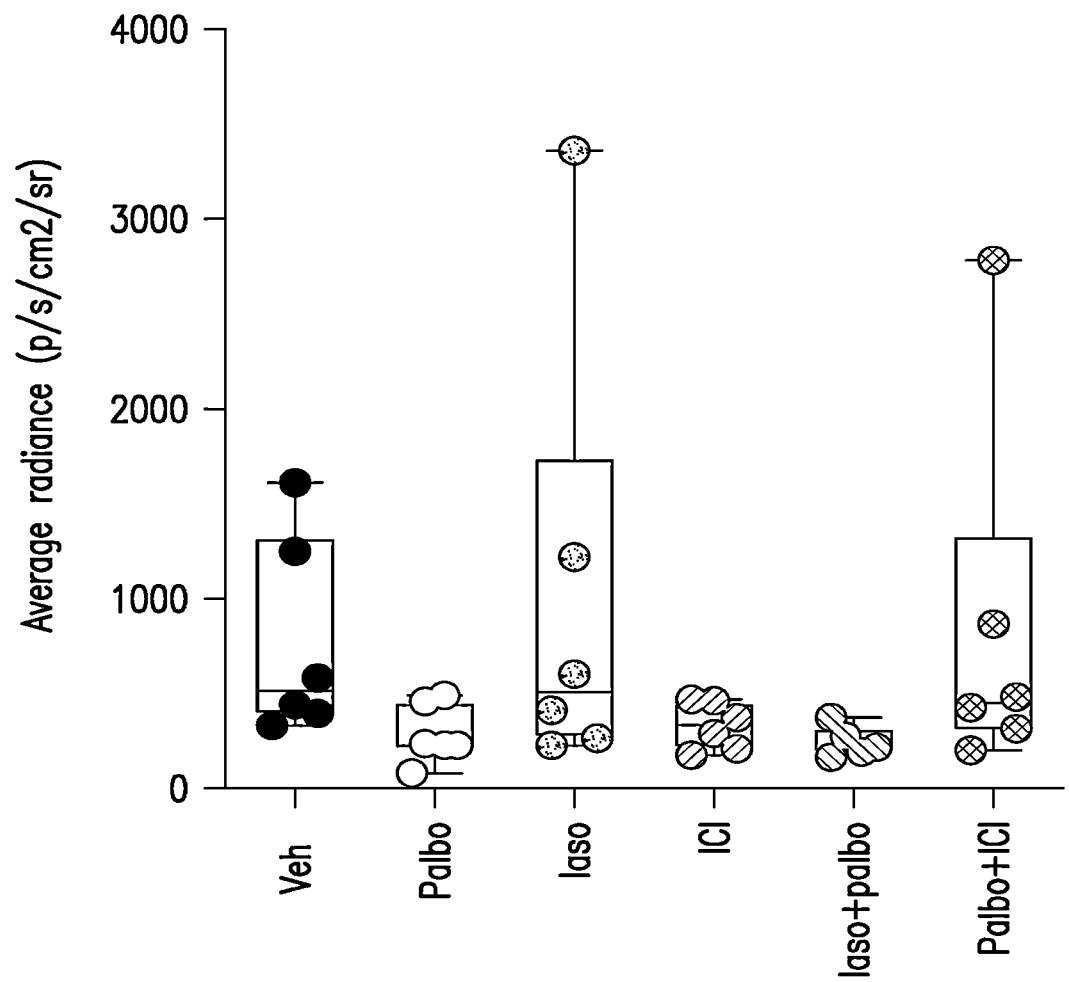
Figure 7B:
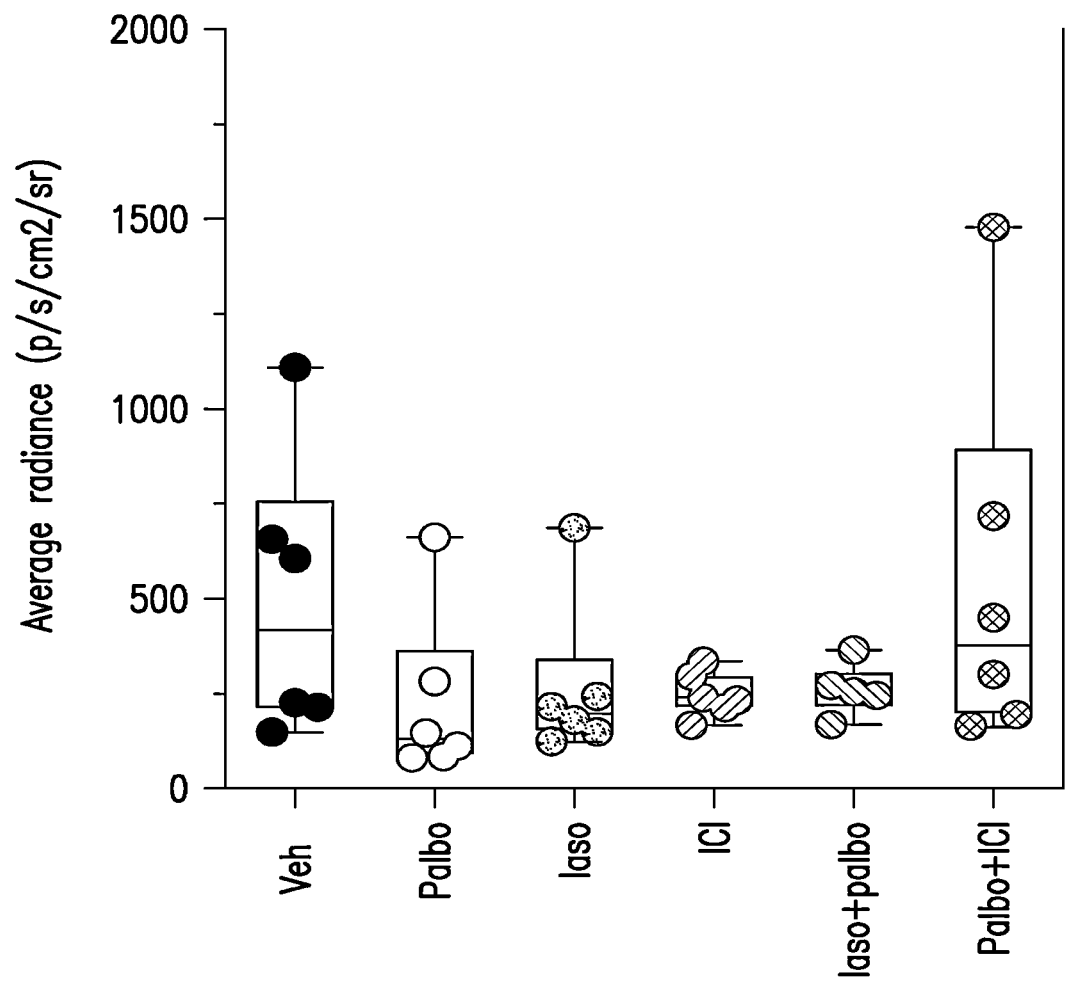
Figure 7C:
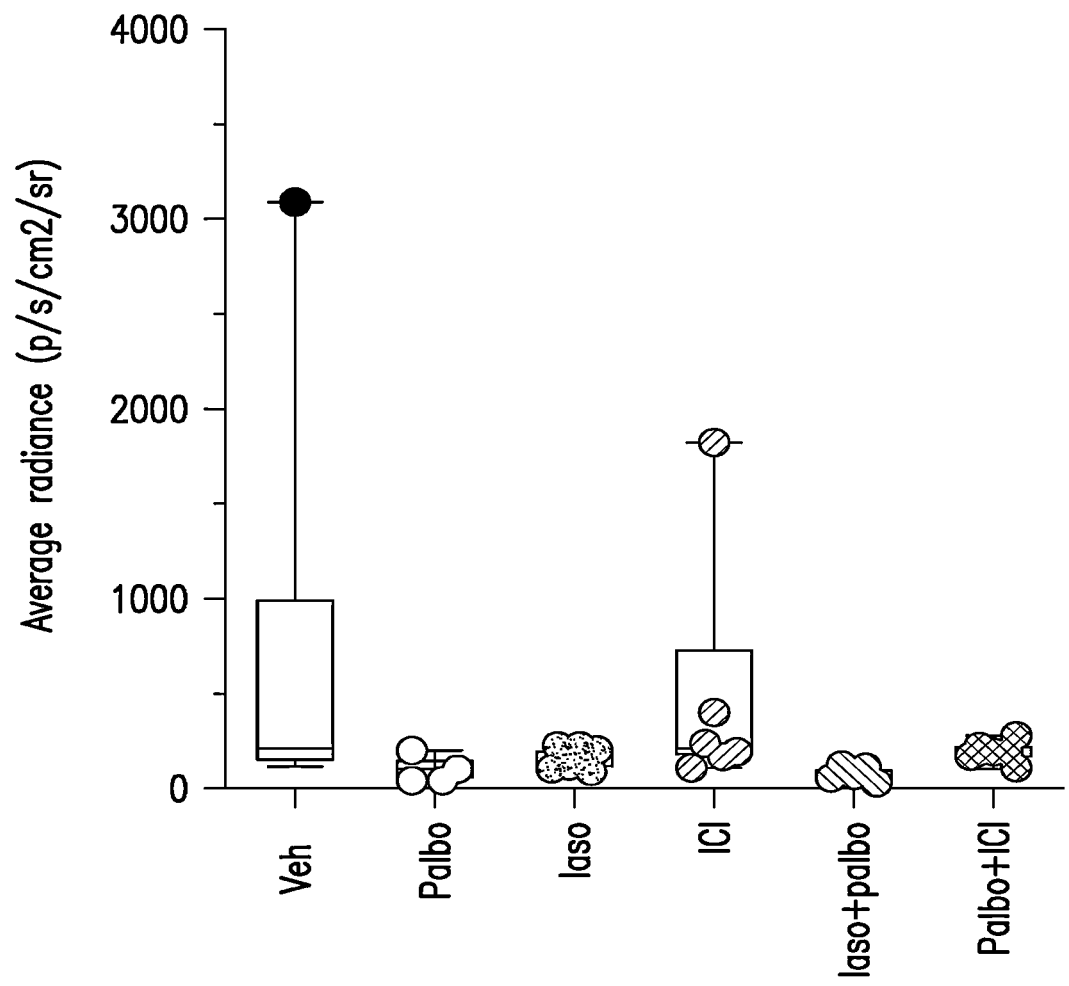

FIGS. 7A-7C present ex vivo radiance measurements in liver, lung and brain. Ex-vivo imaging of excised organs at sacrifice. Radiance was measured in the liver (FIG. 7A), lungs (FIG. 7B), and brain (FIG. 7C). N=3-6 for liver, lungs and brain and N=6-12 for the bones.

Figure 8A:
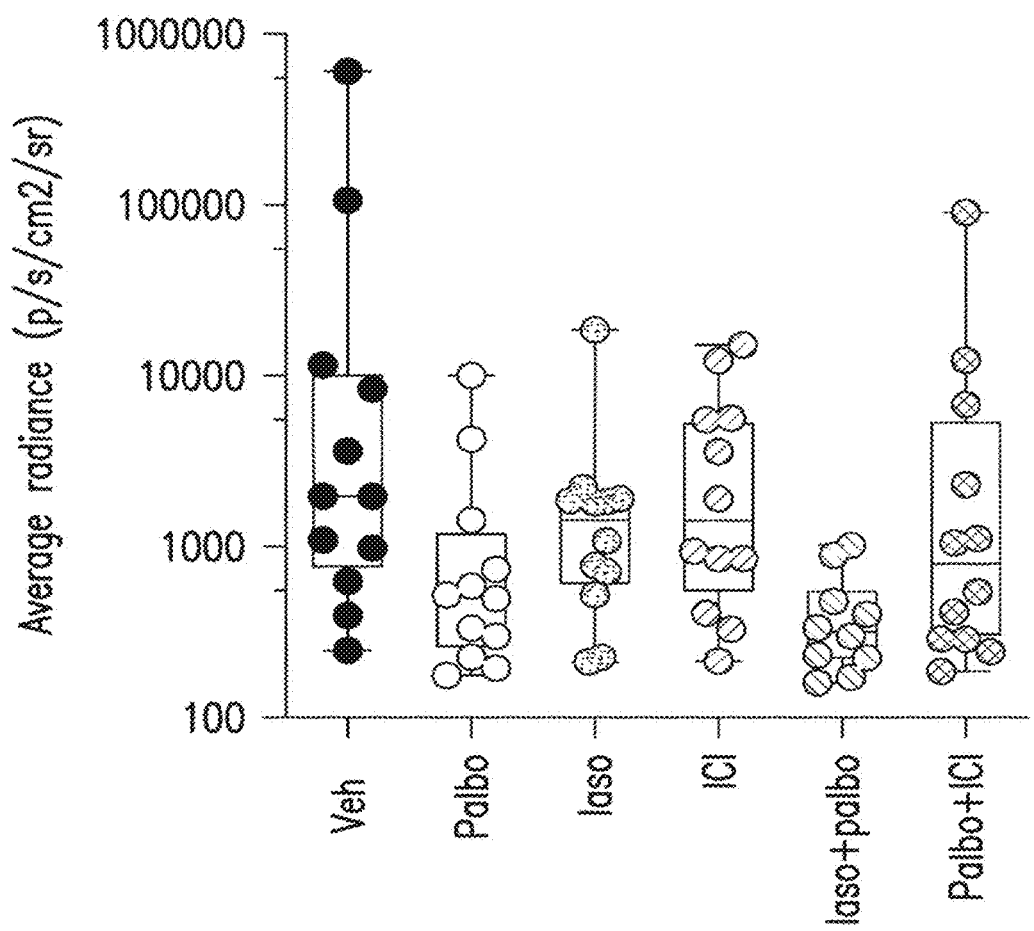
Figure 8B:
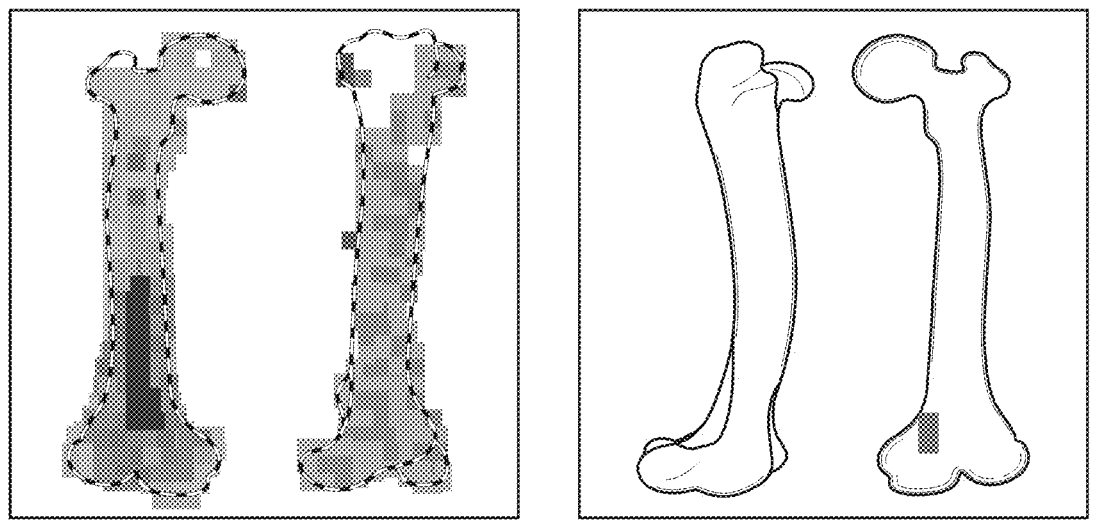

FIGS. 8A-8B present ex vivo radiance measurements in bone. FIG. 8A: Radiance was measured in bones at sacrifice. N=6-12 for the bones. FIG. 8B shows representative images.

Figure 9A:
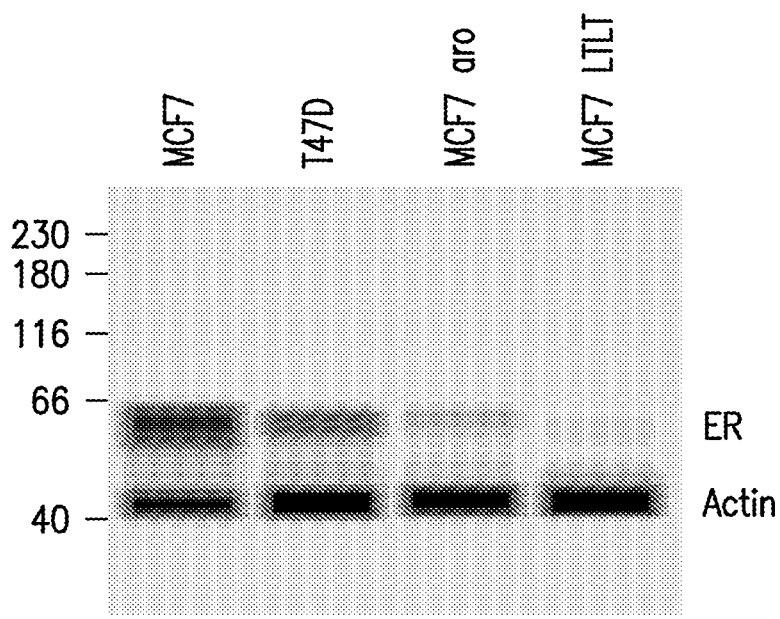
Figure 9B:
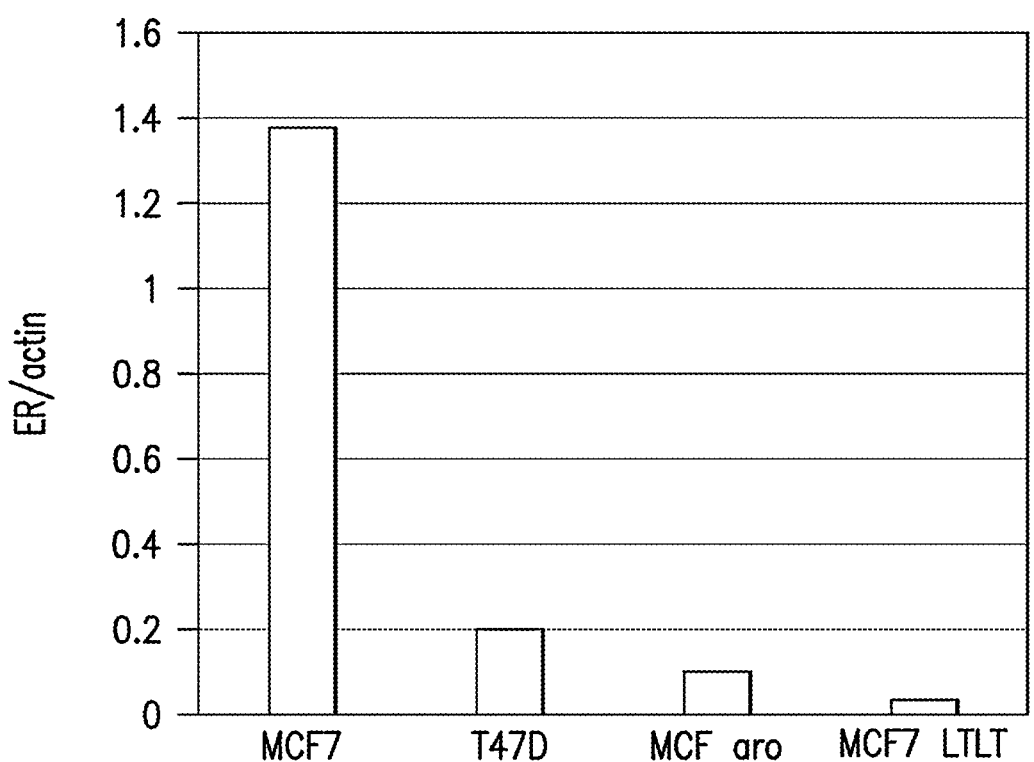
Figure 9C:
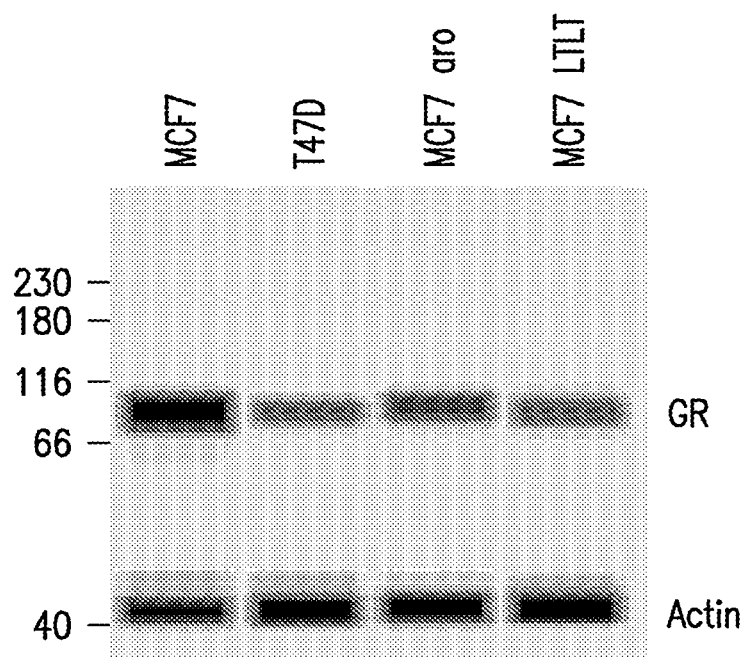
Figure 9D:
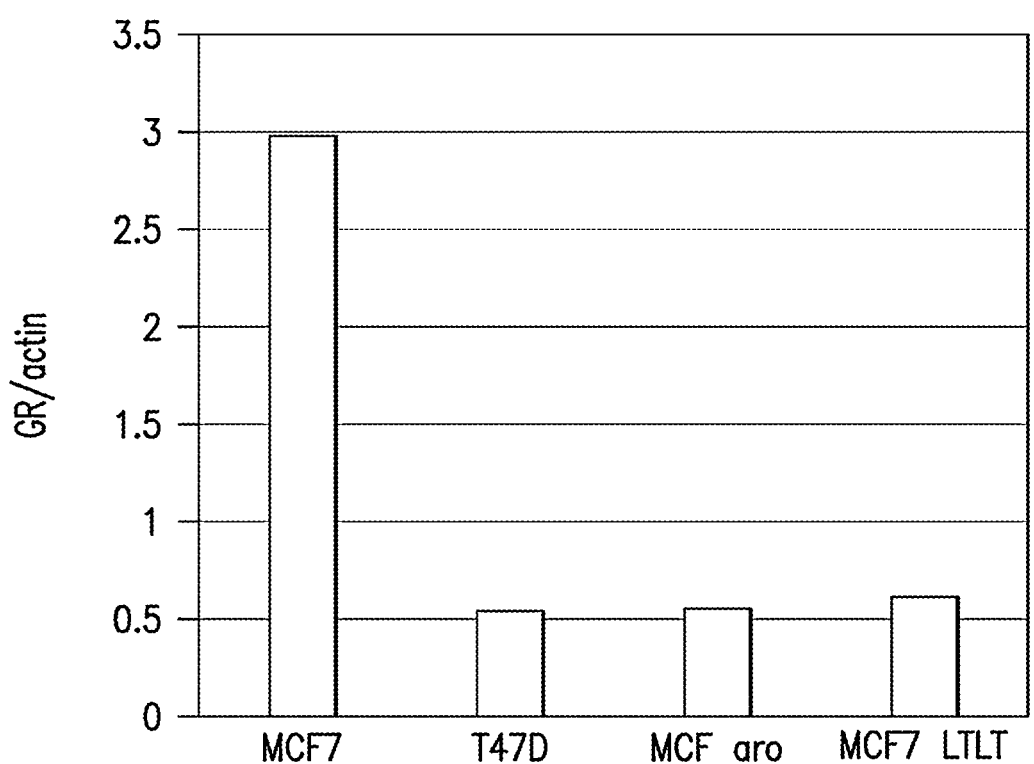

FIGS. 9A-9D present data showing that ERα and glucocorticoid receptor (GR) protein expression is lower in MCF7aro and LTLT compared to MCF7 and T47D. FIG. 9A, western blot showing ERα and actin. FIG. 9B, normalization of ERα levels to actin. FIG. 9C, western blot showing GR and actin. FIG. 9D, normalization of GR protein band to actin.

Figure 10A:
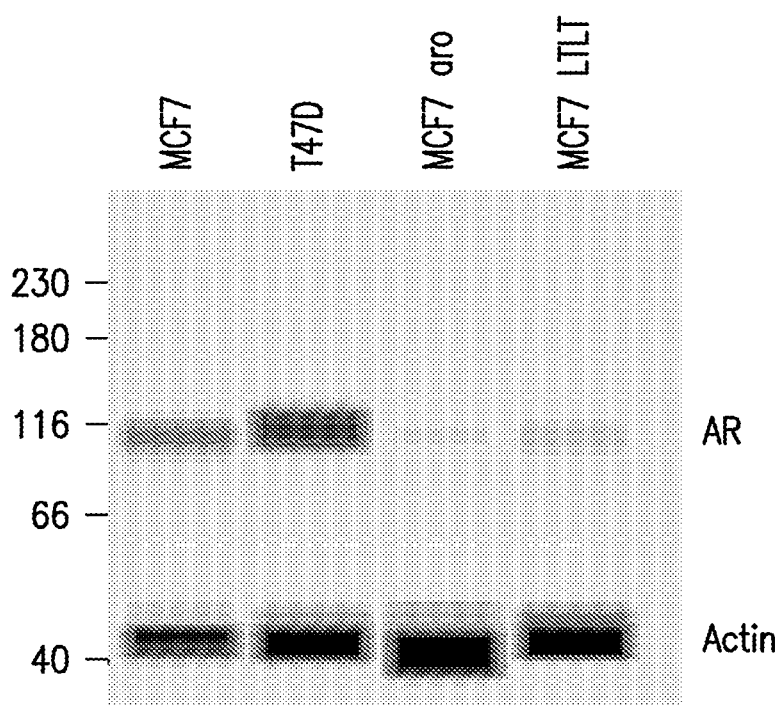
Figure 10B:
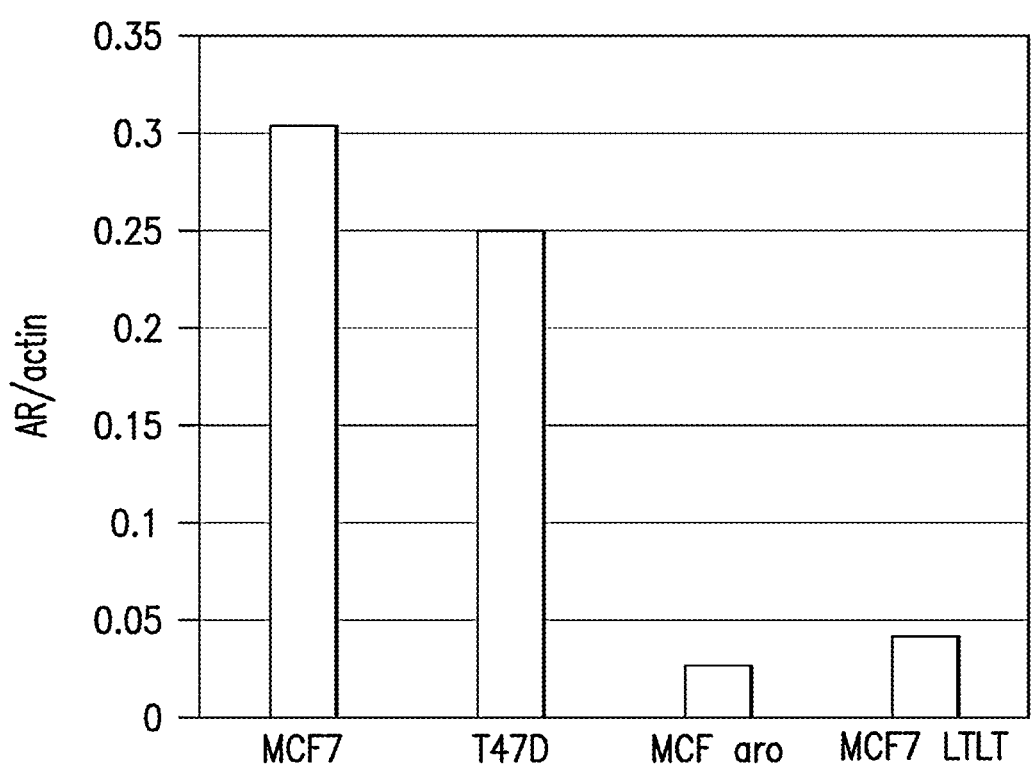
Figure 10C:
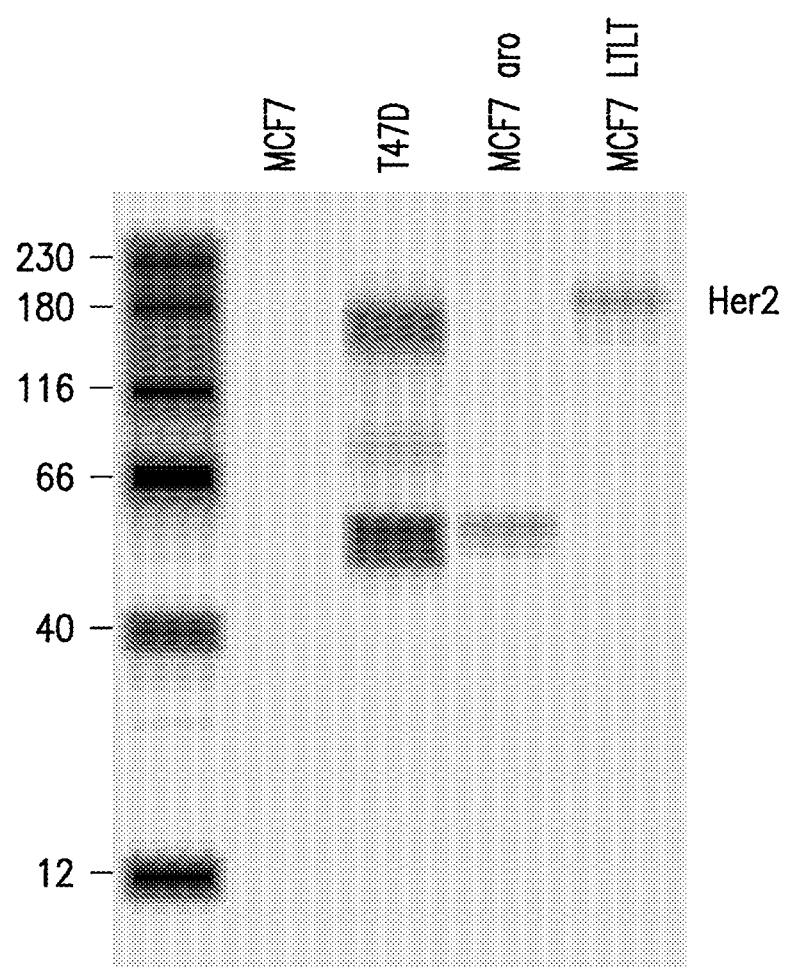
Figure 10D:
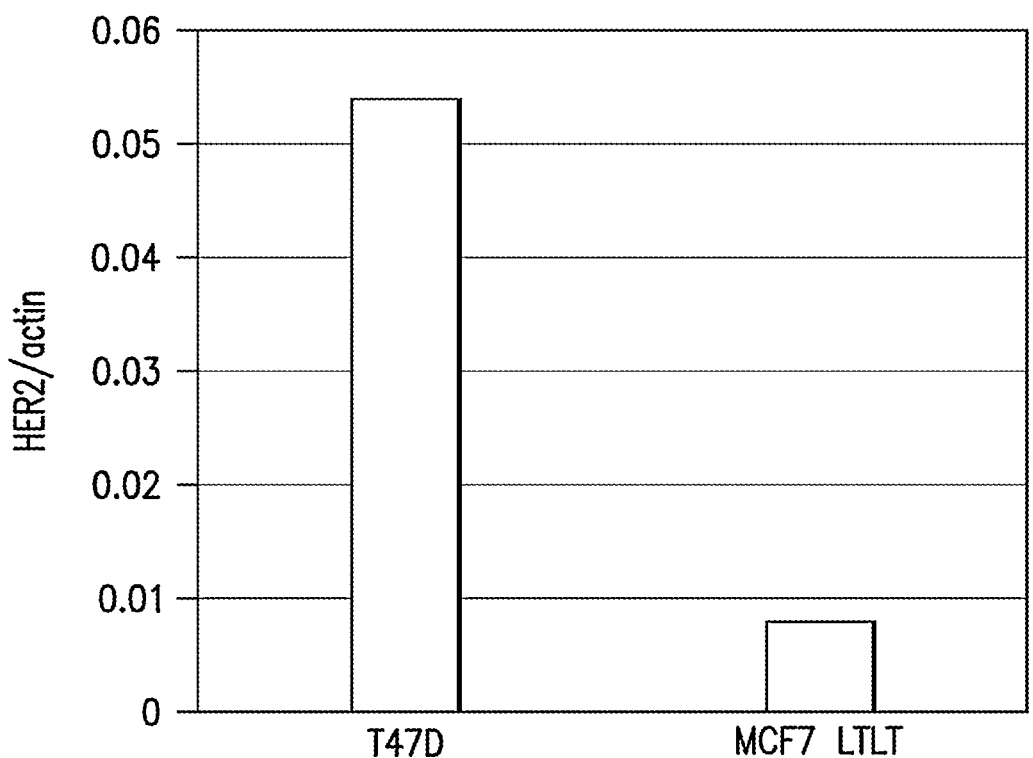
Figure 10E:
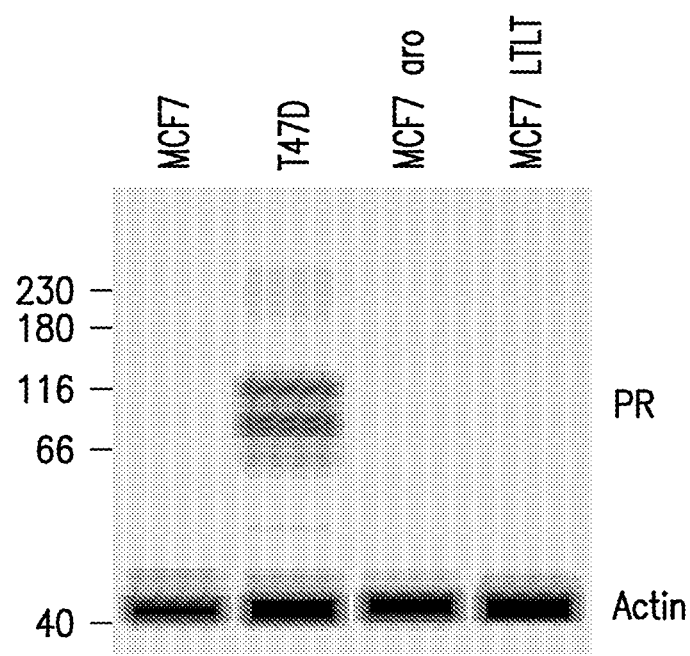

FIGS. 10A-10E present data comparing AR, HER2 and PR protein levels in MCF7aro and MCF7 LTLT compared to MCF7 and T47D. FIG. 10A, western blot showing AR and actin. FIG. 10B, normalization of AR levels to actin. FIG. 10C, western blot showing Her2 expression in MCF7 LTLT. FIG. 10D, normalization of Her 2 to actin for T47D and MCF7 LTLT. FIG. 10E, western blot showing PR. For AR and Her2, one gel was run. For PR, showing one of two representative experiments.

5. DETAILED DESCRIPTION OF THE INVENTION

Postmenopausal patients with estrogen receptor positive (ERα+) primary invasive breast cancer are typically treated with aromatase inhibitors (AIs) as first line adjuvant therapy. Patients who become resistant to AIs are currently treated with the SERD, fulvestrant, and/or with CDK4/6 inhibitors, such as palbociclib, as second line therapy. Lasofoxifene has previously been demonstrated to retain its ability to inhibit progression of ER+ tumors that have become AI-resistant through acquisition of gain-of-function (activating) mutations in the ligand binding domain of the ERα receptor. Lasofoxifene's ability to prevent progression of AI-resistant ER+ cancers that escape endocrine therapy by other mechanisms is unknown.

As described in the examples below, we compared the efficacy of lasofoxifene, both alone and in combination with palbociclib, to fulvestrant, both alone and in combination with palbociclib, in a breast tumor model using letrozole-induced, AI-resistant, cells that do not have activating mutations in the ligand binding domain of the ERα(LTLT cells). Lasofoxifene, alone and in combination with palbociclib, was significantly more effective than fulvestrant, both alone and in combination with palbociclib, in terms of inhibiting primary tumor growth. In addition, all treatments except fulvestrant alone inhibited bone metastasis versus vehicle. These data show that lasofoxifene is more effective than fulvestrant in this tumor model and demonstrate that lasofoxifene is an effective therapy for AI-resistant breast cancers that do not express ERα activating mutations. The data show that the combination of lasofoxifene with a cyclin-dependent kinase 4/6 (CDK4/6) inhibitor is a more effective therapy for AI-resistant breast cancers that do not express ERα activating mutations. Furthermore, lasofoxifene alone or in combination with a cyclin-dependent kinase 4/6 (CDK4/6) inhibitor inhibits metastasis to the bone and to the brain.

5.1. Methods of Treatment

Accordingly, in a first aspect, disclosed herein are methods of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene. The method comprises administering to the patient an effective amount of lasofoxifene or a pharmaceutically acceptable salt, a prodrug, or functional derivative thereof.

In some embodiments, the method further comprises the earlier step of determining that the cancer does not have a gain of function missense mutation within the ligand binding domain (LBD) of the Estrogen Receptor 1 (ESR1) gene.

The methods may comprise administering to the patient an effective amount of lasofoxifene or a pharmaceutically acceptable salt, a prodrug, or functional derivative thereof in combination with a cyclin-dependent kinase 4/6 (CDK4/6) inhibitor, such as palbociclib, abemaciclib or ribociclib, and/or in combination with an aromatase inhibitor, such as exemestane (Aromasin®), letrozole (Femara®), or anastrozole (Arimidex®).

5.1.1. Patient with ER+ Cancer

In various embodiments, the patient has been diagnosed with ER+ cancer. In some embodiments, the ER status has been determined by immunohistochemistry (IHC) performed on a sample of the patient's cancer, by RT-PCR, by massive parallel next generation sequencing (NGS), or by other conventional techniques. In some embodiments, the sample is tumor tissue from a biopsy. In some embodiments, the sample is a liquid biopsy (e.g., serum, circulating DNA of a tumor biomarker) from a blood draw, saliva, or other bodily fluids.

In some embodiments, the patient has been diagnosed with ER+ breast cancer. In some embodiments, the cancer is ER+/HER2− breast cancer. In some embodiments, the patient has been diagnosed with ER+ primary breast cancer. In some embodiments, the cancer is locally advanced or metastatic ER+ breast cancer. In some embodiments, the patient has previously been treated with an aromatase inhibitor selected from exemestane (Aromasin®), letrozole (Femara®), or anastrozole (Arimidex®).

In some embodiments, the patient is premenopausal, perimenopausal or post menopausal. In some embodiments, the patient is premenopausal and has primary ER+ breast cancer. In some embodiments, the patient is premenopausal and has locally advanced or metastatic ER+ breast cancer. In some embodiments, the patient is perimenopausal and has primary ER+ breast cancer. In some embodiments, the patient is perimenopausal and has locally advanced or metastatic ER+ breast cancer. In some embodiments, the patient is postmenopausal and has primary ER+ breast cancer. In some embodiments, the patient is postmenopausal and has locally advanced or metastatic ER+ breast cancer.

In some embodiments, the patient is premenopausal and has primary, or has locally advanced or metastatic ER+ breast cancer, and has previously been treated with an aromatase inhibitor in combination with a second therapy. For example, the patient may have been treated with letrozole in combination with a second therapy such as goserelin (Zeladex®) or leuprolide (Lupron®).

In some embodiments, the patient has been diagnosed with an ER+ cancer other than breast cancer. In some of these embodiments, the patient has been diagnosed with ER+ ovarian cancer. In some of these embodiments, the patient has been diagnosed with ER+ lung cancer. In certain embodiments, the cancer is a gynecological cancer selected from uterine cancer, cervical cancer, peritoneal cancer, vulva cancer, and vaginal cancer.

In some embodiments, the patient has been diagnosed with ER+ primary uterine cancer. In certain embodiments, the uterine cancer is selected from endometrioid, clear-cell carcinoma, papillary serous, carcinosarcoma, leiomyosarcoma, and endometrial stromal sarcoma (ESS). In certain embodiments, the uterine cancer is uterine endometrial stromal sarcoma uterine endometrial adenosarcoma, uterine adenosquamous carcinoma, uterine leiomyosarcoma or uterine corpus carcinoma.

In some of these embodiments, the patient has been diagnosed with ER+ cervical cancer. In certain embodiments, the cervical cancer is cervical clear-cell carcinoma.

In some of these embodiments, the patient has been diagnosed with ER+ vulvar/vaginal cancer. In certain embodiments, the vulva or vaginal cancer is a squamous cell carcinoma (SCC) or an adenocarcinoma.

In some of these embodiments, the patient has been diagnosed with ER+ lung cancer. In certain embodiments, the lung cancer is lung adenosarcoma, squamous cell lung carcinoma, or small cell lung carcinoma.

In certain embodiments, the cancer is a gastrointestinal cancer selected from esophageal cancer, gastric cancer, small intestine cancer, colon cancer, rectal cancer, and colorectal cancer.

In some embodiments, the patient has been diagnosed with ER+ primary esophageal cancer. In certain embodiments, the esophageal cancer is adenocarcinoma or squamous cell carcinoma.

In some embodiments, the patient has been diagnosed with ER+ primary gastric cancer. In certain embodiments, the gastric cancer is gastric adenocarcinoma.

In some embodiments, the patient has been diagnosed with ER+ primary small intestine cancer. In certain embodiments, the small intestine cancer is an adenocarcinoma, carcinoid tumor, lymphoma, or sarcoma such as leiomyosarcoma. In certain embodiments, the small intestine cancer is malignant small intestinal neoplasm.

In some embodiments, the patient has been diagnosed with ER+ primary colon cancer. In certain embodiments, the colon cancer is colon adenocarcinoma.

In some embodiments, the patient has been diagnosed with ER+ primary rectal cancer. In certain embodiments, the rectal cancer is rectal adenocarcinoma.

In some embodiments, the patient has been diagnosed with ER+ primary colorectal cancer. In certain embodiments, the colorectal cancer is colorectal adenocarcinoma and colorectal mucinous adenocarcinoma.

In certain embodiments, the cancer is selected from bladder cancer, e.g., bladder urothelial carcinoma; glioblastoma, e.g., conventional glioblastoma multiforme; skin cancer, e.g., skin squamous cell carcinoma; melanoma, e.g., cutaneous melanoma; infiltrating renal pelvic cancer; pancreatic cancer, e.g., pancreatic adenocarcinoma and cancer of unknown primary origin.

In some embodiments, the ER+ cancer is a primary cancer. In some embodiments, the ER+ cancer is a localized cancer. In some embodiments, the cancer is locally advanced. In some embodiments, the cancer is a metastatic ER+ cancer.

In some embodiments, the patient's cancer has relapsed or progressed after tamoxifen treatment. In some embodiments, the patient's cancer has relapsed or progressed after fulvestrant treatment. In some embodiments, the patient's cancer has relapsed or progressed after aromatase inhibitor treatment. In some of these embodiments, the patient's cancer has relapsed or progressed after multiple lines of endocrine therapy treatment.

5.1.1.1. Detection of the ESR1 Gene Mutations

In various embodiments, the patient has been previously determined not to have a mutation in the LBD of the ESR1 gene. Some embodiments of the methods described herein further include the step of detecting the mutations in ESR1 gene.

In some embodiments, massively parallel next generation sequencing (NGS) is used for detecting the estrogen receptor mutations in the patient's cancer. In certain embodiments, the entire genome is sequenced. In certain embodiments, selected gene panels of cancer-related genes are sequenced. In certain embodiments, all coding exons within a given set of genes are sequenced. In certain embodiments, known "hotspot" regions within a given set of genes are sequenced. However, the inherent error rate of current next generation sequencing techniques is up to 1%, limiting the sensitivity and specificity of detection. In some embodiments, targeted sequencing is used for detecting the presence of the ESR1 mutations. Although targeted sequencing allows deeper sequencing, it is also currently limited by the 1% error rate. In some embodiments, methods with reduced sequencing error rate are used. In a particular embodiment, Safe-Sequencing System (Safe-SeqS) is used, which tags each template molecule to allow for confident identification of rare variants. See Kinde et al., *Proceedings of the National Academy of Sciences* 108(23): 9530-9535 (2011). In particular embodiments, ultrasensitive Duplex sequencing is used, which independently tags and sequences each of the two strands of a DNA duplex. See Schmitt et al., *Proceedings of the National Academy of Sciences* 109(36): 14508-14513 (2012). In some embodiments, digital droplet PCR is used, which emulsifies DNA in thousands to millions of droplets to encapsulate single DNA molecules, designed with mutant specific primers. See Vogelstein and Kinzler,

*Proceedings of the National Academy of Sciences* 96(16): 2322-2326 (1999) and Huggett et al., *Clinical Chemistry* 61(1): 79-88 (2014).

In some embodiments, the detection of the ESR1 mutations takes place at the initial diagnosis. In some embodiments, the detection of the mutations takes place at the time of disease progression, relapse, or recurrence. In some embodiments, the detection of the mutations takes place at the time of disease progression. In some embodiments, the detection of the mutations takes place at the time when the disease is stable.

In some embodiments, one or more tissue specimens are obtained for detection of the mutations. In certain embodiments, the tissue specimen is a tumor biopsy. In certain embodiments, the tissue specimen is a biopsy of metastases. In some other embodiments, liquid biopsies are obtained for detection of the mutations. In certain embodiments, the liquid biopsy is circulating tumor cells (CTCs). In certain other embodiments, the liquid biopsy is cell-free DNA from blood samples.

In specific embodiments, the ESR1 mutations are monitored by circulating tumor DNA (ctDNA) analysis. In some embodiments, the ctDNA analysis is performed throughout the course of treatment. In some of these embodiments, the ctDNA is extracted from patient blood samples. In certain embodiments, the ctDNA is evaluated by digital PCR analysis of the ESR1 mutations.

5.1.2. Adjuvant Treatment

In various embodiments, lasofoxifene is administered to the patient as adjuvant treatment. In certain embodiments, lasofoxifene is administered to the patient as adjuvant treatment alone. In certain other embodiments, lasofoxifene is administered to the patient as adjuvant treatment in combination with other endocrine therapies. In some embodiments, lasofoxifene is administered to the patient after the primary treatment. In some of these embodiments, lasofoxifene is administered to the patient after surgical removal or debulking of the cancer.

In some embodiments, lasofoxifene is administered to the patient as adjuvant therapy in combination with an aromatase inhibitor (AI). In various embodiments, the aromatase inhibitor is exemestane (Aromasin®), letrozole (Femara®), or anastrozole (Arimidex®).

In various embodiments, the aromatase inhibitor predisposes the patient to bone-related toxic effects. In some embodiments, the aromatase inhibitor predisposes the patient to osteoporosis. In some embodiments, the aromatase inhibitor predisposes the patient to bone loss. In some embodiments, the aromatase inhibitor predisposes the patient to bone fractures. In some embodiments, the aromatase inhibitor predisposes the patient to bone pain.

In various embodiments, the aromatase inhibitor predisposes the patient to vulvovaginal atrophy (VVA).

In some embodiments, lasofoxifene is administered continuously during the administration of the aromatase inhibitor. In some other embodiments, lasofoxifene is administered cyclically during the administration of the aromatase inhibitor. In some embodiments, lasofoxifene and the aromatase inhibitor are administered together (simultaneously). In some other embodiments, lasofoxifene and the aromatase inhibitor are administered separately (sequentially).

In certain embodiments, the dosing regimen of lasofoxifene is different from the dosing regimen of the aromatase inhibitor. In some of these embodiments, the dosing quantity of lasofoxifene is different from the dosing quantity of the aromatase inhibitor. In some embodiments, the dosing schedule of lasofoxifene is different from the dosing schedule of the aromatase inhibitor. In some embodiments, the route of administration of lasofoxifene is different from the route of administration of the aromatase inhibitor.

In certain embodiments, the dosing regimen of lasofoxifene is the same as the dosing regimen of the aromatase inhibitor. In some embodiments, the dosing quantity of lasofoxifene is the same as the dosing quantity of the aromatase inhibitor. In some embodiments, the dosing schedule of lasofoxifene is the same as the dosing schedule of the aromatase inhibitor. In some embodiments, the route of administration of lasofoxifene is the same as the route of administration of the aromatase inhibitor.

In some embodiments, lasofoxifene is administered as adjuvant therapy in combination with an aromatase inhibitor to the patient for one year. In some embodiments, lasofoxifene is administered as adjuvant therapy in combination with an aromatase inhibitor to the patient for two years. In some embodiments, lasofoxifene is administered as adjuvant therapy in combination with an aromatase inhibitor to the patient for three years. In some embodiments, lasofoxifene is administered as adjuvant therapy in combination with an aromatase inhibitor to the patient for four years. In some embodiments, lasofoxifene is administered as adjuvant therapy in combination with an aromatase inhibitor to the patient for five years. In some embodiments, lasofoxifene is administered as adjuvant therapy in combination with an aromatase inhibitor to the patient for six years. In some embodiments, lasofoxifene is administered as adjuvant therapy in combination with an aromatase inhibitor to the patient for seven years. In some embodiments, lasofoxifene is administered as adjuvant therapy in combination with an aromatase inhibitor to the patient for eight years. In some embodiments, lasofoxifene is administered as adjuvant therapy in combination with an aromatase inhibitor to the patient for nine years. In some embodiments, lasofoxifene is administered as adjuvant therapy in combination with an aromatase inhibitor to the patient for ten years. In some other embodiments, lasofoxifene is administered as adjuvant therapy in combination with an aromatase inhibitor to the patient for more than ten years. In certain embodiments, lasofoxifene is administered as adjuvant therapy in combination with an aromatase inhibitor until the patient's cancer progresses on therapy.

In some embodiments, lasofoxifene is administered as adjuvant therapy in combination with an aromatase inhibitor to increase the disease-free survival of the cancer patient. In some embodiments, lasofoxifene is administered as adjuvant therapy in combination with an aromatase inhibitor to decrease the incidence of contralateral breast cancer. In some embodiments, lasofoxifene is administered as adjuvant therapy in combination with an aromatase inhibitor to prevent the recurrence or progression of the cancer.

5.2. Lasofoxifene

In various embodiments, the selected patient is treated with an effective amount of lasofoxifene, a pharmaceutically acceptable salt thereof, a prodrug or functional derivative thereof. Lasofoxifene has the following structure:

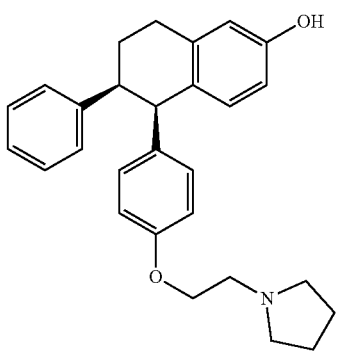 [SMILES: Oc1ccc2c(c1)CC[C@H](c1ccccc1)[C@@H]2c1ccc(OCCN2CCCC2)cc1]

In some embodiments, lasofoxifene is administered to the selected patient as lasofoxifene tartrate.

The term "pharmaceutically acceptable salt" refers to non-toxic pharmaceutically acceptable salts. See Gould, *International Journal of Pharmaceutics* 33: 201-217 (1986) and Berge et al., *Journal of Pharmaceutical Sciences* 66(1): 1-19 (1977). Other salts well known to those in the art may, however, be used. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Embodiments also include prodrugs of the compounds disclosed herein. In general, such prodrugs include functional derivatives of the compounds described herein which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", H. Bundgaard, Elsevier, 1985.

In certain embodiments, a functional derivative of lasofoxifene encompasses a proteolysis targeting chimera (PROTAC) comprising lasofoxifene. In certain embodiments, PROTACS are heterobifunctional small molecules with three chemical elements: lasofoxifene, a ubiquitin ligand binding moiety or ULM group, and a linker for conjugating these two elements. In some embodiments, lasofoxifene is covalently conjugated to a ubiquitin ligand binding moiety or ULM group via a linker. Non-limiting examples of such linkers include ester linkers, amide linkers, maleimide or maleimide-based linkers; valine citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanols acid; linkers that include caproleic acid, and linkers including any combination thereof. In embodiments, the linker is a chemically labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers, oxime-based linkers, carbonate-based linkers, ester-based linkers, etc. In some embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., cancer cell). Enzyme-labile linkers include, but are not limited to, linkers that include peptidic bonds, dipeptide-based linkers such as valine-citrulline linker, such as a maleimidocaproyl-valine-citruline-p-aminobenzyl (MC-vc-PAB) linker, a valyl-alanyl-para-aminobenzyloxy (Val-Ala-PAB) linker, and the like. Chemically-labile linkers enzyme-labile, and non-cleavable linkers are described in detail, e.g., Ducry & Stump (2010) *Bioconjugate Chem.* 21:5-13. In certain embodiments, ULM is selected from the group consisting of:

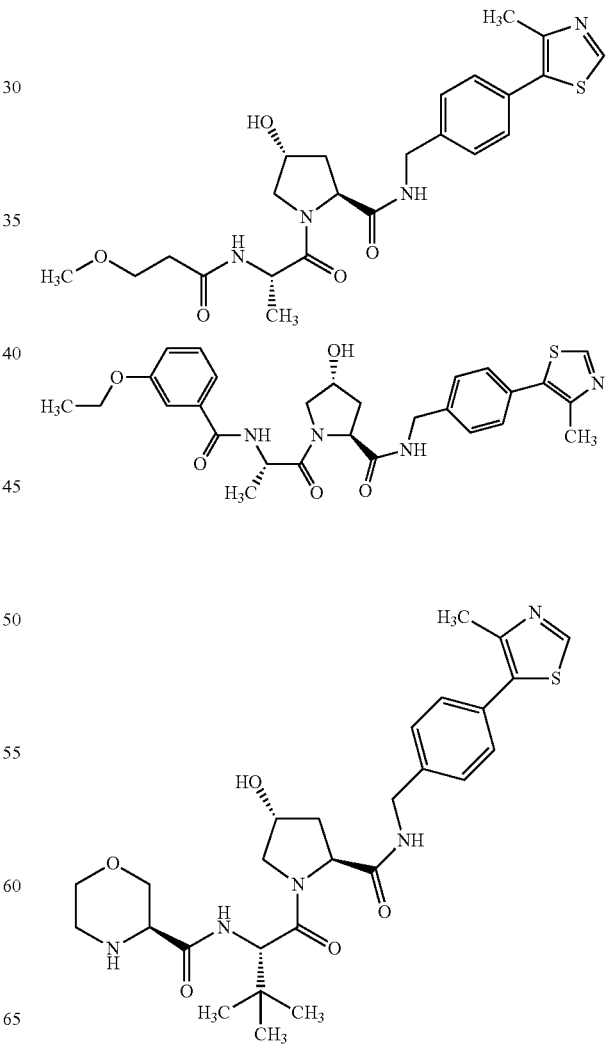

-continued

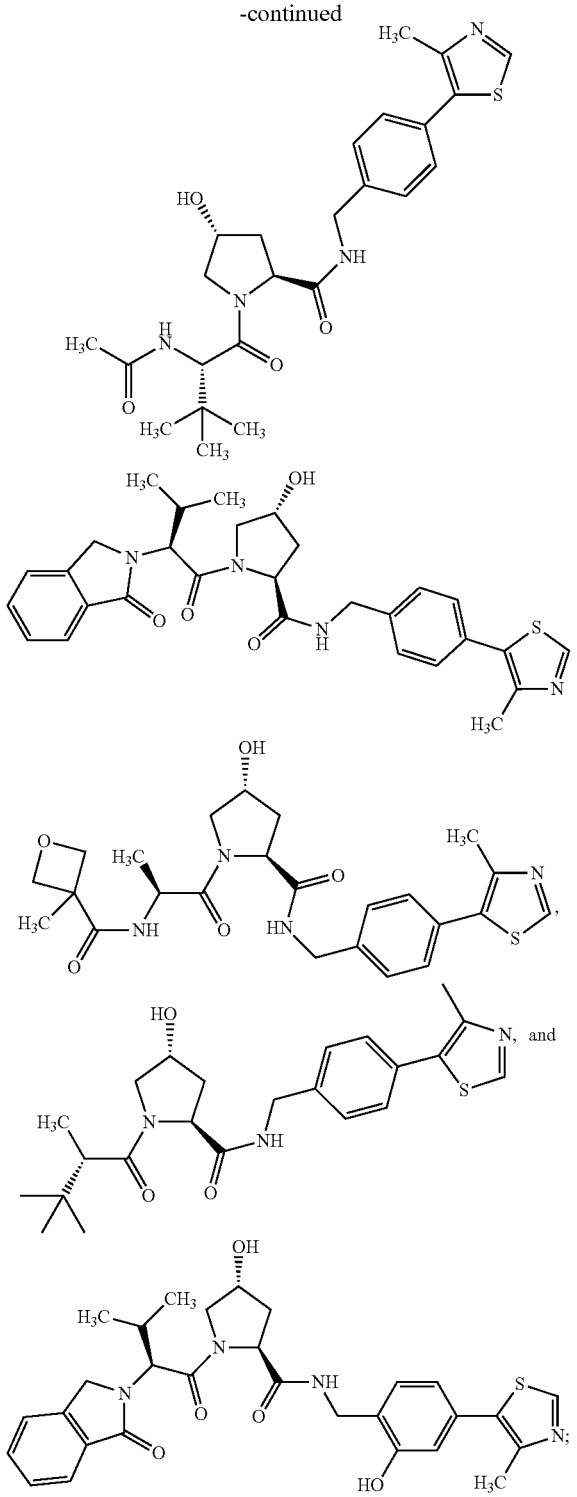

wherein the ULM group is covalently bonded to the linker to which is attached lasofoxifene, or a pharmaceutically acceptable salt, stereoisomer, solvate, polymorph or prodrug thereof.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed by some embodiments.

Where the processes for the preparation of the compounds as disclosed herein give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed by some embodiments.

5.3. Pharmaceutical Compositions

Methods for treatment of estrogen receptor positive (ER$^+$) cancers include administering a therapeutically effective amount of lasofoxifene, a pharmaceutically acceptable salt thereof, a prodrug, or functional derivative thereof. The lasofoxifene, the pharmaceutically acceptable salt, or the prodrug of the invention can be formulated in pharmaceutical compositions. In addition to lasofoxifene, a pharmaceutically acceptable salt thereof, or a prodrug thereof, the composition further comprises a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., oral, intravenous, transdermal, vaginal topical, or vaginal ring.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal oil, vegetable oil, mineral oil or synthetic oil. Physiological saline solution, dextrose or other saccharide solution or glycols such as ethylene glycol, propylene glycol or polyethylene glycol can also be included.

For parenteral administration, the lasofoxifene will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Pharmaceutical compositions for vaginal topical administration can be in the form of ointment, cream, gel or lotion. The pharmaceutical compositions for vaginal topical administration often include water, alcohol, animal oil, vegetable oil, mineral oil or synthetic oil. Hydrocarbon (paraffin), wool fat, beeswax, macrogols, emulsifying wax or cetrimide can also be included.

A composition can be administered alone or in combination with other treatments, either simultaneously or sequentially, dependent upon the condition to be treated.

5.4. Treatment Regimens

In the methods of administering an effective amount of lasofoxifene, a pharmaceutically acceptable salt thereof, a prodrug, or functional derivative thereof, in the form of a pharmaceutical composition as described above for treatment of ER+ cancer, the terms "treatment", "treating", and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

The term "effective amount" means a dose that produces the desired effect for which it is administered. The exact dose will depend on the purpose of the treatment and will be ascertainable by one skilled in the art using known techniques. See Lloyd, *The Art, Science and Technology of Pharmaceutical Compounding* (1999).

5.4.1. Routes of Administration

In various embodiments, lasofoxifene, a pharmaceutically acceptable salt thereof, a prodrug, or functional derivative thereof, is administered by oral, intravenous, transdermal, vaginal topical, or vaginal ring administration.

In some embodiments, lasofoxifene is administered to the patient by oral administration. In certain embodiments, lasofoxifene is administered at about 5 mg/day per os to about 10 mg/day per os, for example, in some embodiments, lasofoxifene is administered at about 5 mg/day per os. In some embodiments, lasofoxifene is administered at about 6 mg/day per os. In some embodiments, lasofoxifene is administered at about 7 mg/day per os. In some embodiments, lasofoxifene is administered at about 8 mg/day per os. In some embodiments, lasofoxifene is administered at about 9 mg/day per os. In some embodiments, lasofoxifene is administered at about 10 mg/day per os. In some embodiments, lasofoxifene is administered to the patient by oral administration (per os) at a dosage of about 0.5 mg/day per os to about 10 mg/day per os, such as about 0.5 mg/day per os to about 5 mg/day per os, about 1 mg/day per os to about 5 mg/day per os, about 2 mg/day per os to about 5 mg/day per os, about 3 mg/day per os to about 5 mg/day per os, about 4 mg/day per os to about 5 mg/day per os, about 0.5 mg/day per os to about 4 mg/day per os, about 1 mg/day per os to about 4 mg/day per os, about 2 mg/day per os to about 4 mg/day per os, about 3 mg/day per os to about 4 mg/day per os, about 0.5 mg/day per os to about 3 mg/day per os, about 1 mg/day per os to about 3 mg/day per os, about 2 mg/day per os to about 3 mg/day per os, about 0.5 mg/day per os to about 2 mg/day per os, about 1 mg/day per os to about 2 mg/day per os, or about 0.5 mg/day per os to about 1 mg/day per os. In some embodiments, lasofoxifene is administered at about 0.5 mg/day per os. In some embodiments, lasofoxifene is administered at about 1 mg/day per os. In some embodiments, lasofoxifene is administered at about 1.5 mg/day per os. In some embodiments, lasofoxifene is administered at about 2 mg/day per os. In some embodiments, lasofoxifene is administered at about 2.5 mg/day per os. In some embodiments, lasofoxifene is administered at about 3 mg/day per os. In some embodiments, lasofoxifene is administered at about 3.5 mg/day per os. In some embodiments, lasofoxifene is administered at about 4 mg/day per os. In some embodiments, lasofoxifene is administered at about 4.5 mg/day per os. In some embodiments, lasofoxifene is administered at about 5 mg/day per os. In some embodiments, lasofoxifene is administered at about 6 mg/day per os. In some embodiments, lasofoxifene is administered at about 7 mg/day per os. In some embodiments, lasofoxifene is administered at about 8 mg/day per os. In some embodiments, lasofoxifene is administered at about 9 mg/day per os. In some embodiments, lasofoxifene is administered at about 10 mg/day per os. In some other embodiments, lasofoxifene is administered at more than 10 mg/day per os. In some embodiments, lasofoxifene is administered at about 0.5 mg/day to about 10 mg/day. In some embodiments, lasofoxifene is administered at about 0.5 mg/day, about 1 mg/day, about 1.5 mg/day, about 2 mg/day, about 2.5 mg/day, about 3 mg/day, about 3.5 mg/day, about 4 mg/day, about 5 mg/day, about 5.5 mg/day, about 6 mg/day, about 6.5 mg/day, about 7 mg/day, about 7.5 mg/day, about 8 mg/day, about 8.5 mg/day, about 9 mg/day, about 9.5 mg/day, or about 10 mg/day. In some embodiments, lasofoxifene is administered orally at about 5 mg/day.

In certain embodiments, lasofoxifene is administered once every day. In certain embodiments, lasofoxifene is administered once every two days. In certain embodiments, lasofoxifene is administered once every three days. In certain embodiments, lasofoxifene is administered once every four days. In certain embodiments, lasofoxifene is administered once every five days. In certain embodiments, lasofoxifene is administered once every six days. In certain embodiments, lasofoxifene is administered once every week. In certain embodiments, lasofoxifene is administered once every two weeks. In certain embodiments, lasofoxifene is administered once every three weeks. In certain embodiments, lasofoxifene is administered once every month.

In some embodiments, lasofoxifene is administered to the patient by vaginal ring administration. In some of these embodiments, lasofoxifene is administered once every two weeks. In some of these embodiments, lasofoxifene is administered once every three weeks. In some of these embodiments, lasofoxifene is administered once every month. In some of these embodiments, lasofoxifene is administered once every two months. In some of these embodiments, lasofoxifene is administered once every three months. In some of these embodiments, lasofoxifene is administered once every four months.

In some embodiments, lasofoxifene is administered to the ER+ breast cancer patient until the patient's cancer progresses on therapy, is in full remission or until the side effects are intolerable.

5.4.2. Combination Therapy

In various embodiments, lasofoxifene, a pharmaceutically acceptable salt thereof, a prodrug, or functional derivative thereof, is administered either alone or in combination with other therapies. In certain embodiments, lasofoxifene is administered in combination with at least one other therapy. In some embodiments, lasofoxifene and other therapies are administered together (simultaneously). In some other embodiments, lasofoxifene and other therapies are administered at different times (sequentially).

In particular embodiments, the additional therapy that the patient is treated with is endocrine therapy. In various embodiments, the patient is treated with at least one line of additional endocrine therapy. In some embodiments, the patient is treated with one line of additional endocrine therapy. In some other embodiments, the patient is treated with multiple lines of additional endocrine therapy. In certain embodiments, the patient's cancer has relapsed or progressed after the previous therapy.

In some embodiments, the patient is treated with the additional endocrine therapy at the original doses. In some other embodiments, the patient is treated with the additional endocrine therapy at doses higher than original doses. In certain embodiments, the patient is treated with the additional endocrine therapy at doses lower than original doses.

In certain embodiments, the additional endocrine therapy is treatment with a selective ER modulator (SERM) other than lasofoxifene. In some of these embodiments, the selective ER modulator is selected from tamoxifen, raloxifene, bazedoxifene, toremifene, and ospermifene, broparestrol, ormeloxifene, OP-1074, and GDC-0945. In certain embodiments, the selective ER modulator is tamoxifen.

In certain embodiments, the additional endocrine therapy is treatment with a selective ER degrader (SERD). In some of these embodiments, the selective ER degrader binds to the estrogen receptor and leads to the proteasomal degradation of the receptor. In some embodiments, the selective ER degrader is selected from fulvestrant, RAD1901 (elacestrant), ARN-810 (GDC-0810), giredestrant (GDC-9545), amcenestrant (SAR439859), rintodestrant (G1T48), LSZ102, LY3484356, zN-c5, D-0502, SHR9549, camizestrant (AZD9833), and AZD9496. In certain embodiments, the endocrine therapy is fulvestrant.

In certain embodiments, the additional endocrine therapy is treatment with an aromatase inhibitor (AI). In some of these embodiments, the aromatase inhibitor is selected from exemestane (Aromasin®), letrozole (Femara®), and anastrozole (Arimidex®).

In some embodiments, the endocrine therapy is ovarian suppression. In various embodiments, the ovarian suppression is achieved by oophorectomy or treatment with a GnRH antagonist. In some embodiments, the ovarian suppression is achieved by treatment with goserelin (Zeladex®) or leuprolide (Lupron®).

In various embodiments, the additional therapy is administration to the patient of an effective amount of a cell cycle inhibitor. In certain embodiments, the additional therapy is administration of an effective amount of cyclin-dependent kinase 4/6 (CDK4/6) inhibitor. In some embodiments, the additional therapy is a CDK4/6 inhibitor selected from the group of palbociclib, abemaciclib, and ribociclib.

In various embodiments, the additional therapy is administration to the patient of an effective amount of a cell cycle inhibitor. In certain embodiments, the additional therapy is administration of an effective amount of AKT kinase inhibitor. In some embodiments, the additional therapy is a AKT inhibitor selected from the group of afuresertib, capivasertib and ipatasertib.

In some embodiments, the additional therapy is administration to the patient of an inhibitor of a pathway that cross-talks with and activates the ER transcriptional activity. In certain embodiments, the additional therapy is a mammalian target of rapamycin (mTOR) inhibitor. In specific embodiments, the mTOR inhibitor is Everolimus. In some of these embodiments, lasofoxifene in combination with Everolimus is administered to a postmenopausal woman with locally advanced or metastatic cancer who has progressed on a non-steroidal AI and/or fulvestrant either as monotherapy or in combination with a CDK4/6 inhibitor. In various embodiments, the additional therapy is a phosphoinositide 3-kinase (PI3K) inhibitor or a heat shock protein 90 (HSP90) inhibitor.

In various embodiments, the additional therapy is administration to the patient of an effective amount of a growth factor inhibitor. In certain embodiments, the additional therapy is a human epidermal growth factor receptor 2 (HER2) inhibitor. In some embodiments, the HER2 inhibitor is trastuzumab)(Herceptin®). In some other embodiments, the HER2 inhibitor is ado-trastuzumab emtansine (Kadcyla®).

In some embodiments, the additional therapy is administering to the patient an effective amount of a histone deacetylase (HDAC) inhibitor. In various embodiments, the HDAC inhibitor is vorinostat (Zolinza®), romidepsin (Istodax®), chidamide (Epidaza®), panobinostat)(Farydak®, belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In certain embodiments, the HDAC inhibitor is entinostat (MS-275) with the proviso that the patient is not treated with a HER2 inhibitor. In certain other embodiments, the HDAC inhibitor is vorinostat (Zolinza®). In yet certain other embodiments, the HDAC inhibitor is romidepsin (Istodax®).

In some embodiments, the additional therapy is administering to the patient an effective amount of a checkpoint inhibitor. In certain embodiments, the checkpoint inhibitor is an antibody. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In some embodiments, the PD-1 antibody is pembrolizumab (Keytruda®) or nivolumab (Opdivo®). In some embodiments, the CTLA-4 antibody is ipilimumab (Yervoy®).

In certain embodiments, the additional therapy is administering to the patient an effective amount of cancer vaccine.

In some embodiments, the additional therapy is administering to the patient an effective amount of denosumab.

In some embodiments, the additional therapy is administering to the patient an effective amount of a serotonin-norepinephrine reuptake inhibitor (SNRI), a selective serotonin reuptake inhibitor (SSRI), or gabapentin. In certain embodiments, the SNRI is venlafaxine (Effexor®).

In some embodiments, the additional therapies described in the preceding paragraphs can be used in combination. Lasofoxifene, a pharmaceutically acceptable salt thereof, a prodrug, or functional derivative thereof, can be administered in combination with two therapies, for example an endocrine therapy such as aromatase inhibitor (e.g. letrozole) and a cell cycle inhibitor such as a CDK4/6 inhibitor (e.g. palbociclib, abemaciclib, and ribociclib).

5.4.3. Clinical Endpoints

5.4.3.1. Primary Clinical Endpoints

In various embodiments, the method comprises administering an amount of lasofoxifene, a pharmaceutically acceptable salt thereof, a prodrug, or functional derivative thereof, effective to increase the disease-free survival of the ER$^+$ cancer patient. In some embodiments, the method comprises administering lasofoxifene in an amount effective to reduce recurrence of ER$^+$ cancer. In some embodiments, the method comprises administering lasofoxifene in an amount effective to increase time to recurrence of ER$^+$ cancer. In some embodiments, the method comprises administering lasofoxifene in an amount effective to reduce metastasis of ER$^+$ cancer. In some embodiments, the method comprises administering lasofoxifene in an amount effective to increase duration of progression-free survival of the ER$^+$ cancer patient.

In various embodiments, the method increases the disease-free survival of the ER$^+$ cancer patient. In certain embodiments, the method reduces recurrence of ER$^+$ cancer. In certain embodiments, the method increases time to recurrence of ER$^+$ cancer. In certain embodiments, the method reduces metastasis of ER$^+$ cancer to bone. In certain embodiments, the method reduces metastasis of ER$^+$ cancer to tissues other than bone. In certain embodiments, the method reduces metastasis of ER$^+$ cancer to the brain. In certain embodiments, the method reduces metastasis of ER$^+$ cancer to the lung. In certain embodiments, the method reduces metastasis of ER$^+$ cancer to the liver. In certain embodiments, the method increases duration of progression-free survival of the ER$^+$ cancer patient. The methods may comprise administering lasofoxifene in combination with one or more additional therapeutic agents, as described herein.

In various embodiments, the method increases the disease-free survival in ER$^+$ cancer patient with AI resistance. In some embodiments, the method reduces recurrence of cancer in patient with AI resistance. In some embodiments, the method increases time to recurrence of cancer in patient with AI resistance. In some embodiments, the method reduces metastasis of cancer in patient with AI resistance. In some embodiments, the method increases duration of progression-free survival in ER$^+$ cancer patient with AI resistance.

In some embodiments, the method increases disease-free survival, reduces recurrence, increases time to recurrence, reduces metastasis, and/or increases duration of progression-free survival in patients with ER$^+$ locally advanced or metastatic cancer that has developed AI resistance. In particular embodiments, the cancer has developed AI resistance by acquiring one or more mutations other than a gain of function mutation in LBD of the ESR1 discussed herein. In some embodiments, the method reduces the selective pressure and prevents the expansion of the AI resistant clones in ER$^+$ locally advanced or metastatic cancer during treatment.

5.4.3.2. Secondary Clinical Endpoints

In some embodiments, the method is effective to prevent fracture and bone loss in women who are concurrently being treated with one or more drugs causing or predisposing to osteoporosis.

In some embodiments, the method is effective to decrease vaginal pH, increase vaginal lubrication, and/or improve vaginal cell maturation index in women who are concurrently being treated with one or more drugs causing or predisposing to vulvovaginal atrophy (VVA).

In some embodiments, the method reduces one or more symptoms of sexual dysfunction in women who are concurrently being treated with one or more drugs causing or predisposing to sexual dysfunction.

In some embodiments, the method treats hot flashes in women who are concurrently being treated with one or more drugs causing or predisposing to hot flashes.

In some embodiments, the method increases one or more quality of life measures selected from joint ache, urogenital symptoms, bone loss, and bone fractures.

EMBODIMENTS OF THE INVENTION

A1a. Lasofoxifene or a pharmaceutically acceptable salt, prodrug, or functional derivative thereof, for use in a method of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene, the method comprising: administering to the patient an effective amount of lasofoxifene or a pharmaceutically acceptable salt, prodrug or functional derivative thereof.

A1b. Lasofoxifene or a pharmaceutically acceptable salt, prodrug, or functional derivative thereof, for use in a method of reducing metastasis of ER$^+$ cancer in a patient who has progressed on an aromatase inhibitor, wherein the cancer does not have a gain of function missense mutation within the ligand binding domain (LBD) of the Estrogen Receptor 1 (ESR1) gene, optionally wherein the method reduces metastasis of ER+ cancer to bone or to the brain, preferably wherein the method reduces metastasis of ER+ cancer to the brain.

A1c. A combination comprising Lasofoxifene or a pharmaceutically acceptable salt, prodrug, or functional derivative thereof, and a cyclin-dependent kinase 4/6 (CDK4/6) inhibitor for separate, simultaneous or sequential use in a method of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene, optionally wherein the combination further comprises an aromatase inhibitor such as letrozole.

A1d. Lasofoxifene or a pharmaceutically acceptable salt, prodrug, or functional derivative thereof, for use treatment of AI-resistant breast cancers that do not express ERα activating mutations.

A1e. A combination comprising Lasofoxifene or a pharmaceutically acceptable salt, prodrug, or functional derivative thereof, and a cyclin-dependent kinase 4/6 (CDK4/6) inhibitor for separate, simultaneous or sequential use in a method of reducing metastasis of ER$^+$ cancer in a patient who has progressed on an aromatase inhibitor, wherein the cancer does not have a gain of function missense mutation within the ligand binding domain (LBD) of the Estrogen Receptor 1 (ESR1) gene, optionally wherein the combination further comprises an aromatase inhibitor such as letrozole.

A2. Lasofoxifene, or a pharmaceutically acceptable salt, prodrug, or functional derivative thereof, for use according to any one of embodiments A1a to A1e, wherein the ER+ cancer is locally advanced or metastatic breast cancer, optionally wherein the cancer is HER2−.

A3. Lasofoxifene, or a pharmaceutically acceptable salt, prodrug, or functional derivative thereof, for use according to any previous embodiment, wherein the aromatase inhibitor is exemestane, letrozole, or anastrozole.

A4. Lasofoxifene, or a pharmaceutically acceptable salt, prodrug, or functional derivative thereof, for use according to any previous embodiment, wherein the method comprises:
(i) determining that the cancer does not have a gain of function missense mutation within the ligand binding domain (LBD) of the Estrogen Receptor 1 (ESR1) gene, and
(ii) administering to the patient an effective amount of lasofoxifene or a pharmaceutically acceptable salt, prodrug, or functional derivative thereof.

A5. Lasofoxifene for use according to any previous embodiment, wherein lasofoxifene is administered as lasofoxifene tartrate.

A6. Lasofoxifene, or a pharmaceutically acceptable salt, prodrug, or functional derivative thereof, for use according to any previous embodiment, wherein lasofoxifene is administered by oral, intravenous, transdermal, vaginal topical, or vaginal ring administration.

A7. Lasofoxifene, or a pharmaceutically acceptable salt, prodrug, or functional derivative thereof, for use according to any previous embodiment, wherein lasofoxifene is administered by oral administration.

A8. Lasofoxifene, or a pharmaceutically acceptable salt, prodrug, or functional derivative thereof, for use according to embodiment A7, wherein lasofoxifene is administered orally in a dose of 5 mg/day to about 10 mg/day.

A9. Lasofoxifene, or a pharmaceutically acceptable salt, prodrug, or functional derivative thereof, for use according to any previous embodiment, wherein the cancer has a mutation in a gene listed in Table 1.

A10. Lasofoxifene, or a pharmaceutically acceptable salt, prodrug, or functional derivative thereof, for use according to any previous embodiment, wherein the method further comprises treating said patient with at least one additional endocrine therapy.

A11. Lasofoxifene, or a pharmaceutically acceptable salt, prodrug, or functional derivative thereof, for use according to any previous embodiment, wherein the method further comprises administering to said patient an effective amount of cyclin-dependent kinase 4/6 (CDK4/6) inhibitor, optionally wherein the CDK4/6 inhibitor is administered orally, e.g. in a dose of 70 mg/kg.

A12. Lasofoxifene, or a pharmaceutically acceptable salt, prodrug, or functional derivative thereof, and a cyclin-dependent kinase 4/6 (CDK4/6) inhibitor for simultaneous, separate or sequential use in a method of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene.

A13. Embodiment A11 or A12, wherein said CDK4/6 inhibitor is palbociclib, abemaciclib, or ribociclib, optionally wherein the CDK4/6 inhibitor is palbociclib, preferably wherein the CDK4/6 inhibitor is abemaciclib.

A14. Lasofoxifene, or a pharmaceutically acceptable salt, prodrug, or functional derivative thereof, for use according to any one of embodiments A1-A10, wherein the method further comprises administering to said patient an effective amount of an AKT inhibitor.

A15. Lasofoxifene, or a pharmaceutically acceptable salt, prodrug, or functional derivative thereof, and an AKT inhibitor for simultaneous, separate or sequential use in a method of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene.

A16. Embodiment A14 or A15, wherein the AKT inhibitor is afuresertib.

A17. Lasofoxifene, or a pharmaceutically acceptable salt, prodrug, or functional derivative thereof, for use according to any one of embodiments A1-A10, further comprising administering to said patient an effect amount of an mTor inhibitor.

A18. Lasofoxifene, or a pharmaceutically acceptable salt, prodrug, or functional derivative thereof, and an mTor inhibitor for simultaneous, separate or sequential use in a method of reducing the progression of estrogen receptor positive (ER+) cancer in a patient who has progressed on an aromatase inhibitor, wherein the cancer does not have a gain of function missense mutation within the ligand binding domain (LBD) of the Estrogen Receptor 1 (ESR1) gene.

5.5. Examples

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of molecular biology, cell biology, biochemistry, genetics, cancer biology, and pharmacology, within the skill of the art. Such techniques are explained fully in the literature.

5.5.1. Example 1: Generation of Letrozole-Induced, AI Resistant, Breast Tumor Model (MCF-7 Cells) that does not Express ERα Activating Mutations Postmenopausal patients with estrogen receptor positive (ERα+) primary invasive breast cancer are typically treated with aromatase inhibitors (AIs) as first line adjuvant therapy. Patients who become resistant to AIs are treated with fulvestrant and/or CDK4/6 inhibitors, such as palbociclib, as second line therapy. Lasofoxifene, a selective estrogen receptor modulator (SERM), was developed for the treatment of vaginal atrophy and osteoporosis. Our previous studies, performed in an MCF-7 xenograft metastatic breast cancer mouse model with activating ERα mutations, showed that lasofoxifene, both alone and in combination with palbociclib, was more effective than fulvestrant at inhibiting tumor growth and metastasis to the liver, lung, bone and brain in the context of gain-of-function activating mutations in the ERα receptor, encoded by the ESR1 gene.

In the current study, we compared the efficacy of lasofoxifene, both alone and in combination with palbociclib, to fulvestrant, alone and in combination with palbociclib, in a breast tumor model using letrozole-induced, AI-resistant, cells that do not express ERα with activating mutations in the ligand binding domain (LTLT cells).

Luciferase-GFP tagged LTLT cells were injected into the mammary ducts of NSG mice (MIND model) and tumor progression was monitored by live luminescence imaging of primary tumors, as well as ex vivo imaging and histochemical analysis of metastatic sites at study endpoint. Primary tumor area was also measured at study endpoint. Lasofoxifene alone and in combination with palbociclib was significantly more effective than fulvestrant, both alone and in combination with palbociclib, in terms of inhibiting primary tumor growth. In addition, all treatments except fulvestrant alone inhibited bone metastasis versus vehicle. These data show that lasofoxifene is more effective than fulvestrant in this tumor model and demonstrate that lasofoxifene is an effective therapy for AI-resistant breast cancers that do not express ERα activating mutations.

Cell Culture, Lentivirus Production and Infection, Generation of Stable Cell Lines MCF 7 LTLT cells, also known as LTLT-Ca cells (Sabnis, G., et al. *Cancer Res.* 69, 1416-1428 (2009)), are derivatives of the hormone receptor positive (ER+, PR+, GR+) human breast cancer cell line, MCF7 which bears WT and mutant ERα. MCF 7 LTLT cells have an acquired resistance to aromatase inhibitors. They were originally derived in the Brodie lab by long term treatment of MCF7aro cells with the aromatase inhibitor, letrozole (Sabnis et al., 2009). MCF-7aro cells are stably transfected with the aromatase gene (Sun, X. Z., et al. *J. Steroid Biochem. Mol. Biol.* 63, 29-36 (1997)). MCF7 LTLT cells were a kind gift of Ganesh Raj from UT Southwestern. MCF7aro cells were kindly provided by Shiuan Chen at City of Hope.

To permit in vivo measurement of tumor cell growth, we transfected MCF 7 LTLT cells with the L2G lentivirus vector (pFU-Luc2-eGFP) containing luciferase and GFP under the control of a ubiquitin promotor (Liu, H., et al. *Proc. Natl Acad. Sci. USA* 107, 18115-18120 (2010)), in suspension at a MOI=5, and plated. Cells were grown in RPMI containing 10% FBS and 1 μM letrozole. For cell studies, MCF 7 LTLT and MCF7aro cells were transfected with the lentivirus nuclear-GFP staining (Nuclight GFP/puro, cat #4475 Essen Bioscience) according to the manufacturer's recommendation.

Assessment of Genotype

To confirm that the aromatase-resistant MCF 7 LTLT cells lack ESR1 ligand binding domain gain-of-function mutations, and to survey non-ESR1 mutations that might confer the endocrine therapy-resistance phenotype on the MCF 7 LTLT cells, we performed whole genome exon sequencing and compared the sequence data to two previously reported MCF7 reference sequences (Ref 1 and Ref 2) (FIG. 1).

The MCF 7 LTLT cells (LT-LT cells in FIG. 1) were determined to lack ESR1 mutations, and to have 18,687 novel variants, among which were 1508 exonic, nonsynonymous, variants. Notable genes having variants (63 genes, 85 variants) are listed in Table 1.

TABLE 1

Notable Genes with Variants (63 genes, 85 variants)

| | | | | |
|---|---|---|---|---|
| TNFRSF1B | CASP3 | ABCA1 | CYP19A1 | NR2F6 |
| RAB42 | DNAH5 | TRAF1 | SETD1A | URI1 |
| FCER1G | LIFR | ABCA2 | CETP | MAP3K10 |
| USH2A | MAP3K1 | MYO3A | CTCF | CYP2F1 |
| MYCN | HSD17B4 | MMP8 | PELP1 | LILRB1 |
| APOB | HLA-A | PTPN6 | TP53 | SRC |
| AFF3 | MYB | KRT18 | DNAH2 | BMP7 |
| VHL | SYNE1 | KRT8 | BCAS3 | GGT1 |
| WNT7A | GLI3 | TPH2 | TMC8 | MN1 |
| RASGEF1B | KMT2C | STAB2 | DSG2 | CYP2D7 |
| PGRMC2 | DEFA3 | FLT3 | SMAD4 | RPGR |
| PALLD | PTPRD | AHNAK2 | MUC16 | |
| NEK1 | SYK | HERC2 | LDLR | |

Phenotypic Characterization of MCF7 LTLT and MCF7aro Via Western Blot.

To characterize the MCF7aro and MCF 7 LTLT cell lines, we performed western blots and probed for ERα, progesterone receptor (PR), androgen receptor (AR) and glucocorticoid receptor (GR).

FIGS. 9A-9D show the relative protein levels of ERα and GR protein in MCF7aro and MCF7 LTLT cells, compared to ERα in normal MCF7 and T47D cells. The expression of actin was used as an internal control for each cell line. As described, MCF7 LTLT cells express less ERα protein than normal MCF7 cells and also less than T47D cells (FIG. 9A), also shown by the ratio of ER to actin expression (FIG. 9B). GR protein levels are lower in MCF7 LTLT and MCF7aro cells, but similar to T47D cells (FIGS. 9C-9D). In both assays, the expression of actin is consistent across cell lines (FIGS. 9A and 9C).

FIGS. 10A-10B show that AR levels are lower in MCF7aro and MCF7 LTLT compared to MCF7 and T47D. FIG. 10C and FIG. 10D show the presence of HER2, which has previously been reported to be upregulated in the MCF7 LTLT cell line. PR was not detected in any of the MCF7, MCF7aro, or MCF7 LTLT cells (FIG. 10E).

5.5.2. Example 2: Efficacy of Lasofoxifene in AI-Resistant Breast Cancer Lacking Gain-of-Function Mutations in the ESR1 Gene Methods For letrozole resistance studies, cells were plated at 2500-3000 cells/well in a 96 well plate either in RPMI or CS RPMI (SRPMI) and treated with various concentrations of letrozole, from 0.1 nM up to 10 μM. For experiments performed in SRPMI, cells were cultured in CS serum for 48 hours prior to treatment. Treatments with estradiol and SERMs (lasofoxifene) were performed in SRPMI. 96 well plates were scanned every 6 hours in an IncuCyte S3 (Essen Bioscience) for up to 1 week. Analyses was performed by counting GFP tagged nuclei via the IncuCyte software.

Animal Studies and Injections

Mouse studies were performed in compliance with an approved Institutional Animal Care and Use Committee protocol. NSG (NOD.Cg-Prkdcscid Il2rgtm1Wjl/SzJ) mice were purchased from The Jackson Laboratories. Prior to injection, mice were anesthetized via inhalation with 2-3% isoflurane in oxygen. Injections of single-cell suspensions of 250,000 MCF7 cells in the mammary ducts of inguinal glands 4 and 9 were performed as described (Behbod, F., et al. *Breast Cancer Res.* 11, R66 (2009); Sflomos, G., et al. *Cancer Cell* 29, 407-422 (2016); Laine, M., et al. *Breast Cancer Res.* 23, 54 (2021)). Tumor growth in situ was followed via imaging in a Xenogen IVIS 200 instrument in the Integrated Small Animal Imaging Research Resource at the University of Chicago. For IVIS imaging, mice were injected with 100 μl of a 0.1 M luciferin solution in PBS (Perkin Elmer XenoLight #122799).

After cell injection, mice were separated into 2 equal groups; one group received 10 μg/day of letrozole in 15% PEG400 in PBS via subcutaneous injection, "LTLT-Let"; the other group wasn't administered letrozole ("LTLT"). Two to three weeks after cell injections, mice in each group were randomized and treated 5 days/week with lasofoxifene (10 mg/kg, in 100 μl of PBS containing 15% PEG400), palbociclib (70 mg/kg, *Med Chem* Express #HY-50567, in 50 mM sodium lactate buffer pH4), or vehicle. Lasofoxifene and vehicle were administered subcutaneously. Palbociclib was administered via oral gavage 5 times/week. Fulvestrant (Med Chem Express #HY-13636) ("ICI") (5 mg/mouse) was administered once per week via subcutaneous injection in 100 μl of mineral oil. Mice were also treated with combinations of lasofoxifene+palbociclib, fulvestrant+palbociclib, lasofoxifene+letrozole and palbociclib or fulvestrant+palbociclib, or letrozole.

TABLE 2

| Treatment | LTLT-Let | LTLT |
|---|---|---|
| Vehicle | + | |
| Lasofoxifene 10.0 mg/kg | + | |
| Fulvestrant 5 mg/week | + | |
| Palbociclib 70 mg/kg | + | |
| Fulvestrant + Palbociclib 70 | + | |
| Lasofoxifene 10 + Palbociclib 70 | + | |
| Vehicle | | + |
| Lasofoxifene 10.0 mg/kg | | + |
| Fulvestrant 5 mg/week | | + |
| Palbociclib 70 mg/kg | | + |
| Fulvestrant + Palbociclib 70 | | + |
| Lasofoxifene 10 + Palbociclib 70 | | + |

After 90-93 days of treatment, mice were sacrificed, and mammary gland tumors were excised and weighed. Liver, bone brain and lungs were removed and imaged ex vivo in the IVIS 200, following an in vivo injection of luciferin 8 min prior to sacrifice, to measure luciferase activity.

IHC and H&E Analyses

Harvested tissues were fixed in formalin for IHC and H&E staining. Tissue histology was performed by the Human Tissue Resource Center (HRTC) at the University of Chicago. Primary Glands excised from the mice were sectioned and stained with antibodies to estrogen receptor alpha (ThermoScientific, RM-9101-S0, clone SP1), progesterone receptor (ThermoScientific, RM-9102-S0, clone SP2), glucocorticoid receptor (Cell Signaling, Cat #3660), androgen receptor (Abcam, ab133273, clone EPR1535), Ki67 (ThermoScientific, Cat #RM-9106-s, Clone: SP6) and human-specific mouse monoclonal antibody to mitochondria (Abcam, ab92824, clone 112-1).

H&E and IHC slides were scanned on a Nikon eclipse Ti2 microscope with a 10× objective for high resolution images. Ki67 score was determined using standardized manual counting.

Western Blot Analysis

Cells were lysed in M-PER lysis buffer (Thermo fisher, cat #78501) in the presence of protease inhibitor cocktail 3 (Calbiochem, cat #535140). Samples were loaded on a WES Protein Simple platform. Antibodies used were: estrogen receptor (Santa Cruz, F10 cat #sc8002), glucocorticoid receptor (Cell signaling, cat #12041s), Her2 (Cell Signaling cat #2242s), androgen receptor (sigma cat #sp242), and progesterone receptor (KD68), an in house generated rat monoclonal antibody (Greene, G. L., et al. *Mol. Endocrinol* 2, 714-726 (1988)).

Graph and Statistical Analysis

Graphs and boxplots were created using Graphpad Prism 7 software. Unpaired, two tailed T-test was used to determined p values.

Results:

Lasofoxifene Alone and in Combination with Palbociclib Inhibits MCF7 LTLT Primary Tumor Growth MCF7 LTLT cells labeled with GFP luciferase were injected into the mammary ducts of NSG mice to establish tumors that represent an AI resistant, non-ESR1-mutated, breast cancer model. Treatment with lasofoxifene, palbociclib and combinations of lasofoxifene and palbociclib were carried out in the presence (Let$^+$) or absence (Let$^-$) of letrozole, to account for the potential loss of letrozole resistance ("reversion") in the Let$^-$ cohort. Mice were imaged every other week in a Xenogen IVIS scanner to estimate tumor growth. At the end of the study, mammary glands were removed and weighed. In this model, tumors were not palpable; however, the total photon flux for vehicle (dark solid circle) and fulvestrant (inversed triangle, also referred to as "ICI") treatments are higher than all other treatments (FIG. 2 and FIG. 3; only Let$^-$ cohorts shown).

Photon flux readings for the different treatment groups, in the presence or absence of letrozole, show a similar pattern, with readings for single treatment with palbociclib or lasofoxifene being 2-3 times lower than vehicle, and readings for the combination of palbociclib and lasofoxifene being 3-4 times lower than vehicle (FIG. 2 and FIG. 3; only Let-cohorts shown). The photon flux for each treatment at day 104, regardless of the presence of letrozole, shows that lasofoxifene, palbociclib, and lasofoxifene+palbociclib is significantly lower than vehicle and fulvestrant (ICI) treatment. Surprisingly, fulvestrant appeared to increase tumor photon flux in the presence of letrozole (data not shown) rather than inhibiting it as expected. This result is currently an unexplained anomaly.

Similar results were observed for mammary gland weights at the end of the study (FIG. 4; only Let$^-$ cohorts shown). However, differences between gland weights are not as dramatic as for radiance (data not shown), likely because these weights include some normal mammary tissue, which dilutes the tumor weight estimates, whereas radiance measurements reflect only luciferase-expressing tumor cells. Regardless, the trend between the weight and radiance is similar, except that fulvestrant does not increase mammary gland weight in either group and in fact inhibits mammary gland weight in the Let$^-$ cohort, but not in the Let$^+$ cohort (data not shown).

FIG. 5 shows tumor area as a percentage (%) of total tissue in the mammary gland, based on H&E staining of a representative section, in the Let$^-$ cohorts. H&E slides were scanned on a Nikon microscope and analyzed with the NSI element software. H&E staining shows that the % tumor area in the Let$^-$ cohort is significantly lower for lasofoxifene alone, compared to vehicle, and that lasofoxifene+palbociclib is significantly lower than vehicle. Palbociclib+fulvestrant (ICI) is also significantly lower than vehicle in the Let$^-$ cohort. Although lasofoxifene+palbociclib appears to be lower than fulvestrant (ICI)+palbociclib, this difference does not reach statistical significance. In the Let$^+$ cohort (data not shown), lasofoxifene+palbociclib is significantly lower than palbociclib+fulvestrant. The other treatments (e.g., palbociclib or fulvestrant alone) did not reach statistical significance versus vehicle or each other.

Given these results, we can conclude that lasofoxifene alone and in combination with the CDK4/6 inhibitor, palbociclib, significantly inhibits primary tumor growth, especially in the Let$^-$ cohort. Overall, the lasofoxifene+palbociclib combination is clearly superior to all other treatments, particularly to the treatment of fulvestrant alone or in combination with palbociclib, which are the conventional treatment regimes. The data indicate that lasofoxifene or lasofoxifene+palbociclib combination is effective in inhibiting primary tumor growth in cancer cells that have developed resistance to letrozole, a commonly prescribed aromatase inhibitor (AI) to treat ER$^+$ breast cancer, through mechanisms other than acquisition of gain-of-function mutations in the ligand binding domain of the ERα receptor (encoded by the ESR1 gene).

Tumor Proliferation Index in the MCF7 LTLT Model is Lower Only in the Letrozole+ Group.

Immunohistochemistry with anti-Ki67 antibody was performed on fixed mammary glands to determine the proliferation index for MCF7 LTLT primary tumors.

Letrozole itself significantly lowers the Ki67 percentage from 56.7+/−9 to 39.5+/−7.7 compared to vehicle (FIG. 6A). Reductions were observed in the Let+ cohort (FIG. 6C), where lasofoxifene alone and lasofoxifene+palbociclib reduce the Ki67 percentage by 6.5% and 12.4% respectively (FIG. 6C and Table 3). Table 3 shows the mean % Ki67 and +/− standard deviation measured manually for each treatment group. Review of the data indicate that the effect of lasofoxifene alone is not significant versus letrozole control, whereas lasofoxifene+palbociclib reduces Ki67 significantly versus palbociclib alone. Interestingly, palbociclib alone or fulvestrant (ICI) alone do not reduce Ki67% levels in this model. However, fulvestrant+palbociclib significantly reduces the Ki67 percentage to 18.8+/−12.3 compared to letrozole control (39.5+/−7.7) and versus palbociclib (45.3+/−19.0) (Table 3). These results suggest that proliferation index alone might not be the best measure of lasofoxifene activity in the MCF7 LTLT model.

TABLE 3

| % Ki67 | | |
|---|---|---|
| | % mean | +/− stdev |
| vehicle | 56.7 | 9.0 |
| palbociclib | 51.7 | 13.4 |
| lasofoxifene | 46.0 | 16.4 |
| fulvestrant (ICI) | 56.8 | 13.4 |
| laso + palbociclib | 53.0 | 8.9 |
| palbociclib + fulvestrant (ICI) | 54.8 | 16.4 |
| letrozole | 39.5 | 7.7 |
| letrozole + palbociclib | 45.3 | 19.0 |
| letrozole + lasofoxifene | 32.7 | 13.1 |
| letrozole + fulvestrant (ICI) | 40.0 | 14.4 |
| letrozole + lasofoxifene + palbociclib | 26.8 | 16.7 |
| letrozole + palbociclib + fulvestrant (ICI) | 18.8 | 12.3 |

Lasofoxifene and Lasofoxifene Plus Palbociclib Appear to Reduce Bone Metastasis

At sacrifice, livers, lungs, bones and brains were excised and imaged ex vivo on the IVIS. FIGS. 7A-7C and FIG. 8A show box plots of the average radiance for liver (FIG. 7A), lung (FIG. 7B), brain (FIG. 7C) and bone (FIG. 8A) in Let− treatment group. Data for Let+ group were evaluated but are not shown. The average radiance for all organs is low, indicating that minimal metastasis was observed. No statistically significant pattern for liver, lung and brain was observed, although the lasofoxifene+palbociclib signal is visually lower in brain than any other treatment versus vehicle for both Let− and Let+ cohorts.

Possible metastasis to the bone was detected (FIG. 8B). However, only 3 readings in the vehicle group, 2 in the fulvestrant (ICI) group, and 1 in the fulvestrant (ICI)+palbociclib group show a signal above threshold. While there appears to be inhibition of radiance versus vehicle for lasofoxifene+palbociclib in both cohorts, especially in the Let− cohort, statistical significance was not reached.

In conclusion, taken together, these data show that for this model of AI resistant breast cancer in which resistance is by mechanisms other than acquisition of ESR ligand binding domain gain-of-function mutations, lasofoxifene alone or in combination with palbociclib inhibits primary tumor growth. In addition, lasofoxifene, alone or in combination with palbociclib, appears to inhibit metastasis to the bone. In general, lasofoxifene combined with palbociclib is more effective than the combination of fulvestrant and palbociclib in primary tumor and metastasis inhibition in these cells. The data has important clinical implications and demonstrate the potential of using lasofoxifene as an effective therapy for women with advanced or metastatic ER+ breast cancers that have become resistant to aromatase inhibitors and that lack ESR1 gain of function mutations.

6. Equivalents and Incorporation by Reference

While the invention has been particularly shown and described with reference to a primary embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method of reducing the progression of estrogen receptor positive and human epidermal growth factor receptor 2 negative (ER+/HER2−) breast cancer in a patient whose breast cancer has progressed on an aromatase inhibitor, wherein the cancer does not have a gain of function missense mutation within the ligand binding domain (LBD) of the Estrogen Receptor 1 (ESR1) gene, the method comprising:
   administering to the patient an effective amount of lasofoxifene or a pharmaceutically acceptable salt thereof.

2. The method of claim 1, wherein the ER+/HER2− cancer is locally advanced or metastatic breast cancer.

3. The method of claim 1, wherein the aromatase inhibitor is exemestane, letrozole, or anastrozole.

4. The method of claim 1, further comprising the earlier step of:
   determining that the cancer does not have a gain of function missense mutation within the ligand binding domain (LBD) of the Estrogen Receptor 1 (ESR1) gene.

5. The method of claim 1, wherein lasofoxifene is administered as lasofoxifene tartrate.

6. The method of claim 5, wherein lasofoxifene tartrate is administered by oral administration.

7. The method of claim 6, wherein lasofoxifene tartrate is administered orally in a dose of 5 mg lasofoxifene/day to about 10 mg lasofoxifene/day.

8. The method of claim 7, wherein lasofoxifene tartrate is administered orally in a dose of 5 mg lasofoxifene/day.

9. The method of claim 1, further comprising administering to said patient an effective amount of a cyclin-dependent kinase 4/6 (CDK4/6) inhibitor.

10. The method of claim 9, wherein said CDK4/6 inhibitor is palbociclib, abemaciclib, or ribociclib.

11. The method of claim 10, wherein the CDK4/6 inhibitor is palbociclib.

12. The method of claim 10, wherein the CDK4/6 inhibitor is abemaciclib.

13. The method of claim 10, wherein the CDK4/6 inhibitor is ribociclib.

14. The method of claim 1, further comprising administering to said patient an effective amount of an AKT inhibitor or mTor inhibitor.

15. A method of reducing the progression of estrogen receptor positive and human epidermal growth factor receptor 2 negative (ER+/HER2−) breast cancer in a patient whose breast cancer has progressed on an aromatase inhibitor, wherein the cancer does not have a gain of function missense mutation within the ligand binding domain (LBD) of the Estrogen Receptor 1 (ESR1) gene, the method comprising:

administering to the patient an effective amount of lasofoxifene or a pharmaceutically acceptable salt thereof in combination with a cyclin-dependent kinase 4/6 (CDK4/6) inhibitor.

16. The method of claim 15, wherein said CDK4/6 inhibitor is palbociclib, abemaciclib, or ribociclib.

17. The method of claim 16, wherein the CDK4/6 inhibitor is palbociclib.

18. The method of claim 16, wherein the CDK4/6 inhibitor is abemaciclib.

19. The method of claim 16, wherein the CDK4/6 inhibitor is ribociclib.

20. The method of claim 15, further comprising the earlier step of:

determining that the cancer does not have a gain of function missense mutation within the ligand binding domain (LBD) of the Estrogen Receptor 1 (ESR1) gene.

21. The method of claim 15, wherein lasofoxifene is administered as lasofoxifene tartrate.

22. The method of claim 21, wherein lasofoxifene tartrate is administered orally in a dose of 5 mg lasofoxifene/day.

23. The method of claim 15, further comprising administering to said patient an effective amount of an AKT inhibitor or an mTOR inhibitor.

24. The method of claim 15, wherein the lasofoxifene and CDK 4/6 inhibitor combination inhibits metastasis of said breast cancer to the bone.

25. A method of reducing the progression of estrogen receptor positive and human epidermal growth factor receptor 2 negative (ER$^+$/HER2$^-$) breast cancer in a patient whose breast cancer has progressed on an aromatase inhibitor, wherein the cancer does not have a gain of function missense mutation within the ligand binding domain (LBD) of the Estrogen Receptor 1 (ESR1) gene, and wherein the cancer has at least one variant in at least one gene set forth in Table 1, the method comprising:

administering to the patient an effective amount of lasofoxifene or a pharmaceutically acceptable salt thereof.

26. The method of claim 25, wherein lasofoxifene is administered as lasofoxifene tartrate by oral administration.

27. The method of claim 26, wherein lasofoxifene tartrate is administered orally in a dose of 5 mg lasofoxifene/day.

28. The method of claim 25, further comprising the earlier steps, in any order, of:

determining that the cancer does not have a gain of function missense mutation within the ligand binding domain (LBD) of the Estrogen Receptor 1 (ESR1) gene, and determining that the cancer has at least one variant in at least one gene set forth in Table 1.

29. The method of claim 25, further comprising administering to said patient an effective amount of a cyclin-dependent kinase 4/6 (CDK4/6) inhibitor.

30. The method of claim 29, wherein said CDK4/6 inhibitor is palbociclib, abemaciclib, or ribociclib.

* * * * *

UNITED STATES PATENT AND TRADEMARK OFFICE
CERTIFICATE OF CORRECTION

PATENT NO. : 12,023,321 B2
APPLICATION NO. : 18/325883
DATED : July 2, 2024
INVENTOR(S) : Komm et al.

It is certified that error appears in the above-identified patent and that said Letters Patent is hereby corrected as shown below:

On the Title Page

Item (54), in Column 1, in "Title", Line 2, delete "ER+CANCER" and insert -- ER+ CANCER --, therefor.

In the Specification

In Column 1, Line 2, delete "ER+CANCER" and insert -- ER+ CANCER --, therefor.

In the Claims

In Column 27, in Claim 24, Line 29, delete "CDK 4/6" and insert -- CDK4/6 --, therefor.

Signed and Sealed this
Fifteenth Day of October, 2024

Katherine Kelly Vidal
*Director of the United States Patent and Trademark Office*